US008492503B2

(12) United States Patent
Culbertson et al.

(10) Patent No.: US 8,492,503 B2
(45) Date of Patent: Jul. 23, 2013

(54) POLYMERIC ALPHA-HYDROXY ALDEHYDE AND KETONE REAGENTS AND CONJUGATION METHOD

(75) Inventors: Sean M. Culbertson, Gurley, AL (US); Xiaoming Shen, Madison, AL (US); Antoni Kozlowski, Huntsville, AL (US); Samuel P. McManus, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 13/063,720

(22) PCT Filed: Sep. 11, 2009

(86) PCT No.: PCT/US2009/005092
§ 371 (c)(1),
(2), (4) Date: May 16, 2011

(87) PCT Pub. No.: WO2010/030366
PCT Pub. Date: Mar. 18, 2010

(65) Prior Publication Data
US 2011/0230618 A1 Sep. 22, 2011

Related U.S. Application Data

(60) Provisional application No. 61/096,112, filed on Sep. 11, 2008.

(51) Int. Cl.
*C08G 12/04* (2006.01)
(52) U.S. Cl.
USPC ........... 528/266; 525/403; 525/405; 525/406; 528/403; 528/405; 528/421
(58) Field of Classification Search
USPC ............... 525/403, 405, 406; 528/403, 405, 528/421, 266
See application file for complete search history.

(56) References Cited

U.S. PATENT DOCUMENTS

| 4,002,531 | A | 1/1977 | Royer |
| 4,044,123 | A | 8/1977 | Daniels et al. |
| 5,252,714 | A | 10/1993 | Harris et al. |
| 5,629,384 | A | 5/1997 | Veronese et al. |
| 5,922,675 | A | 7/1999 | Baker et al. |
| 5,932,462 | A | 8/1999 | Harris et al. |
| 5,990,237 | A | 11/1999 | Bentley et al. |
| 2004/0116649 | A1 * | 6/2004 | Kozlowski ............. 528/230 |
| 2004/0136952 | A1 | 7/2004 | Bhaskaran et al. |
| 2005/0031576 | A1 | 2/2005 | McManus et al. |

FOREIGN PATENT DOCUMENTS

| WO | WO 96/11953 | 4/1996 |
| WO | WO 96/40749 | 12/1996 |
| WO | WO 99/45964 | 9/1999 |
| WO | WO 2004/022630 | 3/2004 |
| WO | WO 2004/060406 | 7/2004 |
| WO | WO 2004/091494 | 10/2004 |
| WO | WO 2007/009208 | 1/2007 |
| WO | WO 2007/140282 | 12/2007 |
| WO | WO 2008/015099 | 2/2008 |

OTHER PUBLICATIONS

Fujita, Y., et al.; Thermochimica Acta, 1995, vol. 253, p. 117-125.*
Amadori, "Prodotti di condensazione tra glucosio e p-fene-tidina," Atti. acad. nazl. Lincei, vol. 2, Series 6, pp. 337-342, (1925).
Amadori, "Prodotti di condensazione tra glucosio e p-fene-tidina," Atti. accad. nazl. Lincei., vol. 9, Series 6, pp. 68-73, (1929).
Amadori, "Prodotti di condensazione tra glucosio e p-ani-sidina," Atti. acad.nazl. Lincei., vol. 9, Series 6, pp. 226-233, (1929).
Crestia, et al, "Chemoenzymatic synthesis of chiral substituted acrylate and acrylonitrile precursors for the synthesis of . . . ," Tetrahedron: Asymmetry, vol. 12, pp. 869-876, (2001).
Heindel, et al, "Hydrazide Pharmaceuticals as Conjugates to Polyaldehyde Dextran: Syntheses, Characterization, and Stability," Bioconj. Chem., vol. 1, pp. 77-82, (1990).
Hermanson, et al, "Modifications of Sugars, Polysaccharides, and Glycoconjugates," Bioconj. Tech., pp. 37-38, (1996).
Hodge, "The Amadori Rearrangement," Advan. Carbohyd. Chem., vol. 10, pp. 169-205, (1955).
Isbell, et al, "Mutarotation, Hydrolysis, and Rearrangement Reactions of Glycosylamines," J. Org. Chem., vol. 23, pp. 1309-1319, (Sep. 1958).
Lemieux, "Rearrangements and Isomerizations in Carbohydrate Chemistry," Mol. Rearrangements, pt. 2, pp. 709-763, (1964).
Micheel, et al, "Der Mechanismus Der Amadori-Umlagerung," Ann., vol. 658, pp. 120-127, (1962).
Ouchi, et al., "Design of Antitumor Agent-Terminated Poly(Ethylene Glycol) Conjugate as Macromolecular Prodrug," Polymer Preprints, vol. 38, No. 1, pp. 582-583, (1997).
Sagara, et al, "A new synthesis of galactose-poly(ethylene glycol)-polyethylenimine for gene delivery to hepatocytes," J. of Contrl. Rel., vol. 79, pp. 271-281, (2002).
Veronese, et al, "PEGylation, successful approach to drug delivery," Drug Disc. Today, vol. 10, No. 21, pp. 1451-1458, (Nov. 2006).
Walton, et al., "3'-Deoxynucleosides. I. A Synthesis of 3'-Deoxyadenosine," J. Am. Chem. Soc., vol. 86, No. 14, pp. 2952, (1964).

(Continued)

*Primary Examiner* — Robert Jones, Jr.
(74) *Attorney, Agent, or Firm* — Mark A. Wilson

(57) ABSTRACT

Provided herein are polymeric α-hydroxy aldehyde or α-hydroxy ketone reagents which can be conjugated to amine-containing compounds to form stable conjugates in a single-step reaction. In selected embodiments, the polymeric reagent itself incorporates an internal proton-abstracting (basic) functional group, to promote more efficient reaction. The substituent is appropriately situated, via a linker if necessary, to position the group for proton abstraction, preferably providing a 4- or 5-bond spacing between the abstracting atom and the hydrogen atom on the α-carbon. Also provided are methods of using the reagents and stable, solubilized conjugates of the reagents with biologically active compounds. In preferred embodiments, the polymeric component of the reagent or conjugate is a polyethylene glycol.

10 Claims, 6 Drawing Sheets

OTHER PUBLICATIONS

Weygand, "Uber N-Glykoside, II. Mitteil: Amadori-Umlagerungen," Atti. acad. nazl. Lincei, No. 11, pp. 1259-1278, (1940).

Wrodnigg, et al, "The Amadori and Heyns Rearrangements: Landmarks in the History of Carbohydrate Chemistry or Unrecognized Synthetic Opportunities?," Top. in Curr. Chem., vol. 215, pp. 115-152, (2001).

PCT International Search Report corresponding to PCT Application No. PCT/US2009/005092 date of mailing Jul. 11, 2011.

PCT International Preliminary Report on Patentability corresponding to PCT Application No. PCT/US2009/005092 date of mailing Jul. 28, 2011.

Enzon Pharmaceuticals, Macromolecular Engineering Technologies, 16 pages, (2004).

NEKTAR™—Transforming Therapeutics, Nektar Molecule Engineering: Polyethylene Glycol and Derivatives for Advanced PEGylation, 24 pages, Catalog—2003, (Jul. 2003).

NEKTAR™—Transforming Therapeutics, Nektar Advanced PEGylation: Polyethylene Glycol and Derivatives for Advanced PEGylation, 27 pages, Catalog—2004, (Jul. 2004).

NEKTAR™—Transforming Therapeutics, Nektar Advanced PEGylation: Polyethylene Glycol and Derivatives for Advanced PEGylation, 33 pages, (Catalog 2005—2006).

NOF Corporation, PEG Derivatives, Phospholipid and Drug Delivery Materials for Pharmaceuticals, pp. 1-46, Catalogue 2003-1st, (Jan. 2003).

NOF Corporation, PEG Derivatives, Phospholipid and Drug Delivery Materials for Pharmaceuticals, pp. 1-50, Catalogue 2003-2nd, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; BIOTINS, 5 pages, (Apr. 2004).

Polypure Products, PEG amines; PEG acids and amino acids; PEG thiols and disulfides; BIOTINS, 5 pages, (Apr. 2005).

Quanta Biodesign, Labeling, Derivatization and Crosslinking Reagents for Biological and Related Materials with dPEG™, pp. 1-38, (Mar. 12, 2004).

Quanta Biodesign, Labeling, Modification and Crosslinking Reagents incorporating our unique monodispersed dPEG™ Technology, pp. 1-31, (Nov. 5, 2004).

Quanta Biodesign, LTD., Leading innovator, producer and provider of monodisperse discrete PEG™ (dPEG™) derivatives, (Product Catalog), pp. 1-51, (Updated: Jul. 18, 2005).

Quanta Biodesign, LTD., Leading innovator, producer and provider of monodisperse discrete PEG™ (dPEG™) derivatives, (Product Catalog), pp. 1-51, (Updated: Nov. 17, 2005).

Shearwater Polymers, Inc., Polyethylene Glycol and Derivatives, 50 pages, (Catalog—Mar. 1995).

Shearwater Polymers, Inc., Polyethylene Glycol and Derivatives, 55 pages, (Catalog—Jul. 1997).

Shearwater Polymers, Inc., Polyethylene Glycol and Derivatives: Functionalized Biocompatible Polymers for Research and Pharmaceuticals, pp. 1-50, (Catalog—Jan. 2000).

Shearwater Corporation, Polyethylene Glycol and Derivatives for Biomedical Applications, 20 pages, (Catalog—Jul. 2001).

\* cited by examiner 1 2 3 4 5 6 7 8

1 2 3 4 5 6 7 8 9 10

1 2 3 4 5 6 7 8 9 10

1 2 3 4 5 6 7 8 9 10

POLYMERIC ALPHA-HYDROXY ALDEHYDE AND KETONE REAGENTS AND CONJUGATION METHOD

CROSS-REFERENCE TO RELATED APPLICATIONS

This application is a 35 U.S.C. §371 application of International Application No. PCT/US2009/005092, filed Sep. 11, 2009, designating the United States, which claims benefit of priority under 35 U.S.C. §119(e) to U.S. Provisional Patent Application Ser. No. 61/096,112, filed 11 Sep. 2008, all of which are incorporated by reference herewith in their entireties.

REFERENCES

Crestia, D. et al., *Tetrahedron: Asymmetry* 12:869-876 (2001).
Hermanson, G. T. *Bioconjugate Techniques*, Academic Press, San Diego, 1996, pp. 37-38.
Hodge, J. E., *Advan. Carbohyd. Chem.* 10:169 (1955).
Isbell, H. S. et al., *J. Org. Chem.* 23:1309 (1958).
Lemieux, R. U., in P. de Mayo, *Molecular Rearrangements*, Pt. 2, p. 753 (1964).
Micheel et al., *Ann.* 658:120 (1962).
Wrodnigg, T. M and Eder, B., *Topics in Current Chemistry* 215:115-152 (2001).

BACKGROUND OF THE INVENTION

In recent years, human therapeutics have expanded past traditional small molecule drugs and into the realm of biopharmaceuticals. The discovery of novel proteins and peptides has led to the development of numerous protein and polypeptide biopharmaceuticals. Unfortunately, proteins and polypeptides, when utilized as therapeutics, often exhibit properties that make them extremely difficult to formulate or administer, such as short circulating half lives, immunogenicity, proteolytic degradation, and low solubility. One approach for improving the pharmacokinetic or pharmacodynamic properties of biopharmaceuticals is the conjugation to natural or synthetic polymers, such as polyethylene glycol (PEG). The covalent attachment of PEG to a therapeutic protein can provide a number of advantages, such as (i) shielding antigenic epitopes of the protein, thus reducing its reticuloendothelial clearance and recognition by the immune system, (ii) reducing degradation by proteolytic enzymes, and (iii) reducing renal filtration.

Much effort has been spent on the development of polymer derivatives for coupling to biopharmaceuticals such as peptides, and in particular, on the development of polymer derivatives for coupling to reactive amino groups of proteins. Examples of such PEG derivatives include PEG dichlorotriazine, PEG tresylate, PEG succinimidyl carbonate, PEG carbonylimidazole, and PEG succinimidyl succinate. However, these reagents can suffer from drawbacks such: undesirable side reactions under the reaction conditions necessary to effect coupling, lack of selectivity, and/or the formation of weak (i.e., unstable) linkages between the biopharmaceutical and the PEG.

Aldehyde-terminated PEGs, such as PEG propionaldehyde and PEG acetaldehyde (see, for Example, U.S. Pat. Nos. 5,252,714 and 5,990,237, respectively) provide the advantage of selectivity in their attachment chemistry. However, when a polymeric aldehyde or ketone is used for conjugation with a polypeptide or similar molecule having a reactive amine group, it is necessary to include a reduction step to stabilize the imine linkage that forms during the conjugation step.

SUMMARY

In one aspect, the invention provides a polymeric reagent having the structure I:

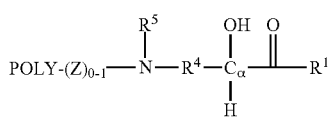

where
$R^1$ is selected from H, lower alkyl, and alkoxyalkyl, and is preferably H or methyl;
$R^4$ is a two- or three-carbon chain which may be substituted with one or more groups selected from alkyl, alkenyl, aryl, alkoxy, halo, cyano, and a water soluble polymer, wherein the carbon adjacent to $C\alpha$ is not substituted with hydroxy, and wherein two substituents on $R^4$ may together form an aliphatic or aromatic ring; and
$NR^5$ is a secondary or tertiary amino group which is linked to a water soluble polymer POLY, preferably a polyethylene glycol, via an optional spacer group Z, where $R^5$ is hydrogen or an alkyl group, which may form a ring with spacer group Z.

In one embodiment, $R^1$ is H, such that the reagent contains an α-hydroxy aldehyde.

In further embodiments, $R^4$ in structure I is unsubstituted or is substituted with lower alkyl. $R^4$ in structure I is preferably a three-carbon chain, and may be saturated or unsaturated. More particularly, reagents in which $R^4$ is a saturated three-carbon chain may have the structure Ia:

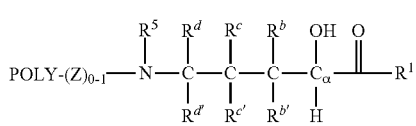

where $R^1$, $NR^5$, Z and POLY are as defined above, each of the substituents $R^c$, $R^{c'}$, $R^d$, and $R^{d'}$ is independently selected from hydrogen, alkyl, alkenyl, aryl, alkoxy, halo, cyano, hydroxy, and a water soluble polymer, and each of the substituents $R^b$ and $R^{b'}$ is independently selected from hydrogen, alkyl, alkenyl, aryl, alkoxy, halo, cyano, and a water soluble polymer, wherein at most one of these substituents is a water soluble polymer, and wherein any two of these substituents can together form an aliphatic ring.

In selected embodiments of this structure, the substituents $R^b$, $R^{b'}$, $R^c$, $R^{c'}$, $R^d$, and $R^{d'}$ are independently selected from hydrogen and alkyl, wherein any two such alkyl substituents, preferably on adjacent carbon atoms, can together form a 5- to 7-membered aliphatic ring.

In one embodiment, the group $R^5$ is methyl. Reagents of this class include those designated (5) and (10) herein (5-(mPEG-methyl-amino)-2-hydroxypentanal). In these exemplary reagents, each of $R^b$, $R^{b'}$, $R^c$, $R^{c'}$, $R^d$, and $R^{d'}$ in structure Ia is hydrogen.

The spacer group Z, when present, preferably consists of bonds selected from alkylene, ether, thioether, amide, and amine. In one embodiment, $NR^5$ together with Z forms a ring to which POLY is linked, e.g. a piperazine ring to which POLY is linked via a ring nitrogen atom. Reagents of this class include those designated (11) and (12) herein (5-mPEG-piperazine-2-hydroxy-pentanal). In these exemplary reagents, each of $R^b$, $R^{b'}$, $R^c$, $R^{c'}$, $R^d$, and $R^{d'}$ in structure Ia is hydrogen.

In another aspect, the invention provides a polymeric reagent having the structure II:

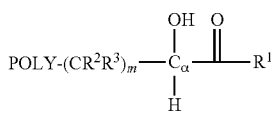

where

POLY is a water soluble polymer, preferably a polyethylene glycol, which may include a linker moiety, as described herein, linking it to $(CR^2R^3)_m$;

$R^1$ is selected from H, alkyl, hydroxyalkyl, and alkoxyalkyl, preferably H or methyl, and more preferably H;

m is 0-12, preferably 0 to 6; and each $R^2$ and $R^3$ is independently selected from H, alkyl, alkylene, hydroxy, amino, alkoxy, hydroxyalkyl, alkoxyalkyl, alkoxyalkylene, aminoalkyl, iminoalkyl, carboxylic acid, alkylcarboxylic acid, phosphate, alkylphosphate, and a further water soluble polymer, wherein at most one $R^2$ or $R^3$ group is a water soluble polymer, and wherein two substituents $R^2$ and $R^3$ in $(CR^2R^3)_m$ can together form a ring;

with the proviso that no $R^2$ or $R^3$ on the carbon adjacent to Cα is a hydroxyl group or a 1,2,3-trihydroxypropyl group.

Preferably, at most one group $R^2$ or $R^3$ is selected from aminoalkyl, iminoalkyl, carboxylic acid, alkylcarboxylic acid, phosphate, and alkylphosphate. Aminoalkyl and iminoalkyl can include (cyclic amino)alkyl or (cyclic imino)alkyl; i.e. where the amine nitrogen is included in a ring, which may itself form part of the —$(CR^2R^3)_m$— chain.

In further preferred embodiments, one group $R^2$ or $R^3$ is selected from hydroxy, alkoxy, hydroxyalkyl, alkoxyalkyl, alkoxyalkylene, amino, aminoalkyl, iminoalkyl, carboxylic acid, alkylcarboxylic acid, phosphate, and alkylphosphate; and preferably from amino, aminoalkyl, iminoalkyl, carboxylic acid, and alkylcarboxylic acid; and this group ($R^2$ or $R^3$) and the value of m are selected such that an oxygen or nitrogen atom on $R^2$ or $R^3$ is separated from Cα by a four-bond path.

In one embodiment, POLY is mPEG-O—, m is 3, and —$(CR^2R^3)_m$— is selected from —$(CH_2)_3$— and —$CH_2$—CH(OH)—$CH_2$—. The compound designated 4 herein (5-mPEG-2-hydroxypentanal) is an example of such a structure where —$(CR^2R^3)_m$— is —$(CH_2)_3$—.

Reagents in which —$(CR^2R^3)_m$— include the moiety —$CH_2$—CH(OH)—$CH_2$— attached to Cα are based on 3-deoxy analogs of reducing sugars, such as 3-deoxy ribose. One example is the compound mPEG-O—$CH_2$—CH(OH)—$CH_2$—CH(OH)—C(O)H, designated herein as 13. Other possible reagents include those derived from the 3-deoxy analogs of, for example, xylose, arabinose, glucose, galactose, or mannose. Five-carbon sugars such as ribose, xylose, and arabinose are preferred. Such reagents are advantageous over the corresponding derivatives of the native sugars, because the absence of the 3-hydroxyl group in the eventual conjugated product reduces opportunities for degradation of the conjugated product.

In another embodiment, POLY is mPEG-O—, m is 1, $R^1$ is H, $R^2$ is H, and $R^3$ is iminoalkyl. The compound designated 3 herein is an example of such a structure, where $R^3$ is (4-imidazolyl)methyl.

In still further embodiments, —$(CR^2R^3)_m$— in structure II is defined by —$CH_2$—$CHR^x$—$C(NH_2)R^y$—, where $R^x$ and $R^y$ form a 5- to 7-membered aliphatic ring to which POLY is linked. Such reagents include those illustrated as follows, where n is 0 to 2:

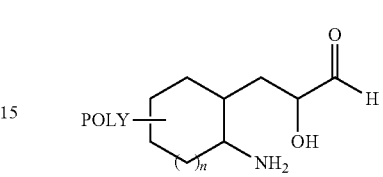

The amino group may be replaced with methylamino or dimethylamino. Reagents similar to those illustrated above but including an aromatic ring are also provided, as described further below.

As noted above, a linker moiety may be used to connect the polymer component POLY to the functional portion of the reagent of structure II, or to connect polymer segments making up the component POLY. The nature of the linker, when present, is described further below. Typically, a linker includes a functional group such as an amide, an ester, a urethane, or a urea, optionally containing methylene or other alkylene groups flanking either side of the single functional group. Alternatively, a linker can be an alkylene chain, optionally containing one or more oxygen or sulfur atoms (i.e., an ether or thioether).

In a related aspect, the invention provides a polymeric α-hydroxy aldehyde or ketone reagent having the structure III:

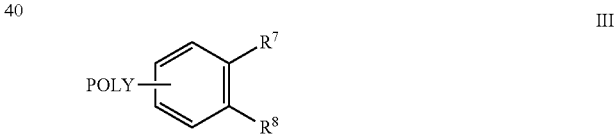

where

POLY is a water soluble polymer, such as a polyethylene glycol, which may include a linker moiety, as described herein, linking it to the aromatic ring; and (i) $R^7$ is —CH(OH)—C(=O)—$R^1$, and $R^8$ is selected from —C(=O)OH, —$CH_2OH$, —C(=O)N($R^1$)$_2$, —$CH_2N(R^1)_2$, —OH, and —N($R^1$)$_2$, and is preferably selected from —C(=O)OH, —$CH_2OH$, —C(=O)N($R^1$)$_2$, and —$CH_2N$($R^1$)$_2$; or (ii) $R^7$ is —$CHR^1CH(OH)$—C(=O)—$R^1$, and $R^8$ is —OH or —N($R^1$)$_2$;

where each $R^1$ is independently selected from H, lower alkyl, and alkoxyalkyl, and is preferably independently selected from H and methyl. In selected embodiments, $R^1$ attached to C(=O) is H, such that the reagent contains an α-hydroxy aldehyde. In other embodiments, each $R^1$ is H.

Exemplary reagents of this class include the compounds designated herein as 6, where $R^7$ is —CH(OH)—C(=O)—H and $R^8$ is —C(=O)OH; 7, where $R^7$ is —CH(OH)—C(=O)—H and $R^8$ is —OH; and 8, where $R^7$ is —$CH_2CH$(OH)—C(=O)—H and $R^8$ is —OH. Analogous reagents include those in which the phenolic hydroxy group (OH) is replaced by $NH_2$ or $N(CH_3)_2$ (that is, $R^8$ is —$NH_2$ or —$N(CH_3)_2$).

In another aspect, the invention provides a method of conjugating a water soluble polymer with a compound B—$NH_2$ having a reactive amine group, the method comprising contacting the compound B—$NH_2$ with a polymeric reagent comprising a water soluble polymer and an α-hydroxy aldehyde or α-hydroxy ketone end group, respectively, thereby forming a conjugate in which the water soluble polymer is linked to a moiety having the structure —C(=O)—$CHR^1$—NH—B, where $R^1$ is hydrogen or methyl, respectively, and NH—B represents the residue of the amine-containing compound. Such contacting is carried out in a suitable aqueous or organic solvent, under conditions as needed for reaction, including catalysis if necessary.

In preferred embodiments, the polymeric reagent further comprises a proton-abstracting functional group containing a proton-abstracting atom selected from oxygen and nitrogen, situated such there is a 3- or 4-bond spacing, preferably a 4-bond spacing, between the proton-abstracting atom and the α-carbon of the α-hydroxy aldehyde or α-hydroxy ketone. Such reagents are able to undergo a "self-catalyzed" conjugation reaction, as described further below.

In selected embodiments, the method employs a polymeric reagent of structure I/Ia, II, or III as described herein.

Additional preferred embodiments of the method generally employ preferred embodiments of the reagents I/Ia, II and III as described herein. The amine-containing compound is typically a biologically active or biologically relevant compound, such as a polypeptide or protein.

In a related aspect, the invention provides conjugates which can be formed by such a method. For example, the invention provides a polymeric conjugate having the structure IV:

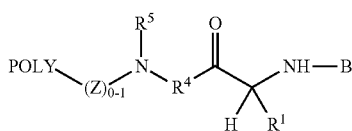

where $R^1$ is selected from H, lower alkyl, and alkoxyalkyl, and is preferably H or methyl;

$R^4$ is a two- or three-carbon chain which may be substituted with one or more groups selected from alkyl, alkenyl, aryl, alkoxy, halo, cyano, and a water soluble polymer, wherein the carbon adjacent to the carbonyl carbon is not substituted with hydroxy, and wherein two substituents on $R^4$ may together form an aliphatic or aromatic ring; and $NR^5$ is a secondary or tertiary amino group which is linked to a water soluble polymer POLY, such as a polyethylene glycol, via an optional spacer group Z, where $R^5$ is hydrogen or an alkyl group, which may form a ring with spacer group Z; and —NH—B represents the residue of an amine-containing biologically active compound.

Selected embodiments of the conjugate include those which correspond to selected embodiments of reagent I/Ia described herein.

Further conjugates of the invention include those of structure V:

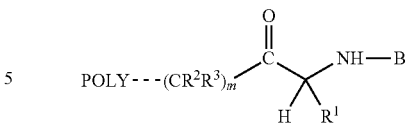

wherein:

POLY is a water soluble polymer, such as a PEG, which may include a linker moiety, as described herein, linking it to $(CR^2R^3)_m$;

$R^1$ is selected from H, alkyl, hydroxyalkyl, and alkoxyalkyl;

m is 0-12; and each $R^2$ and $R^3$ is independently selected from H, alkyl, alkylene, hydroxy, amino, alkoxy, hydroxyalkyl, alkoxyalkyl, alkoxyalkylene, aminoalkyl, iminoalkyl, carboxylic acid, alkylcarboxylic acid, phosphate, alkylphosphate, and a further water soluble polymer, wherein at most one $R^2$ or $R^3$ group is a water soluble polymer, and wherein two substituents $R^2$ and $R^3$ in $(CR^2R^3)_m$ can together form a ring, preferably an aliphatic ring; and —NH—B represents the residue of an amine-containing biologically active compound, such as a polypeptide or protein.

Preferably, no $R^2$ or $R^3$ on the carbon adjacent to the carbonyl carbon is a hydroxyl group or a 1,2,3-trihydroxypropyl group.

Additional preferred embodiments of the conjugate generally correspond to preferred embodiments of the reagent II as described herein.

Further conjugates of the invention include those of structure VI:

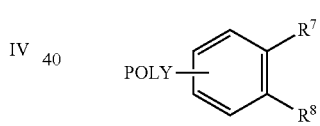

where (i) $R^7$ is C(=O)—$CHR^1$—NH—B, and $R^8$ is selected from —C(=O)OH, —$CH_2$OH, —C(=O)N($R^1$)$_2$, —$CH_2$N($R^1$)$_2$, —OH, and —N($R^1$)$_2$, and is preferably selected from —C(=O)OH, —$CH_2$OH, —C(=O)N($R^1$)$_2$, and —$CH_2$N($R^1$)$_2$; or (ii) $R^7$ is —$CHR^1$—C(=O)—$CHR^1$—NH—B, and $R^8$ is —OH or —N($R^1$)$_2$;

POLY is a water soluble polymer, such as a PEG, which may include a linker moiety, as described herein, linking it to the aromatic ring; and —NH—B represents the residue of an amine-containing biologically active compound;

where each $R^1$ is independently selected from H, lower alkyl, and alkoxyalkyl, and preferably from H and methyl.

Additional preferred embodiments of the conjugate generally correspond to preferred embodiments of the reagent III as described herein, where the groups $R^7$ and $R^8$ are defined accordingly.

In the conjugates of structures IV, V, and VI, the amine-containing compound is typically a biologically active or biologically relevant compound, such as a polypeptide or protein.

These and other aspects of the invention will become apparent upon review of the following description and accompanying figures.

BRIEF DESCRIPTION OF THE DRAWINGS

FIG. 5A, Barium/Iodine stain;
FIG. 5B, Coomassie stain.
Lane:
1) MW markers,
2) 1 μg mPEG$_{20K}$-HP-ALD (9),
3) 3 μg unmodified 55 kDa protein,
4) mPEG$_{20K}$-HP-ALD (9)/55 kDa protein; pH 6.5,
5) mPEG$_{20K}$-HP-ALD (9)/55 kDa protein; pH 7.5,
6) mPEG$_{20K}$-HP-ALD (9)/55 kDa protein; pH 9.0,
7) 1 μg mPEG$_{20K}$-HP-MALD (10),
8) 3 μg unmodified 55 kDa protein,
9) mPEG$_{20K}$-HP-MALD (10)/55 kDa protein; pH 6.5,
10) mPEG$_{20K}$-HP-MALD (10)/55 kDa protein; pH 7.5,
11) mPEG$_{20K}$-HP-MALD (10)/55 kDa protein; pH 9.0,
12) Blank.

FIG. 6A: reactions at r.t. for 1 day;
FIG. 6B, reactions at 5° C. for 1 day.
Lane:
1) Lyz+mPEG$_{20K}$-HP-ALD (9), pH 6.5,
2) Lyz+mPEG$_{20K}$-HP-ALD (9), pH 9.0,
3 Lyz+mPEG$_{20K}$-MAHP (10), pH 6.5,
4) Lyz+mPEG$_{20K}$-MAHP (10), pH 9.0,
5) Lyz+mPEG$_{20K}$-Pip-HP-ALD (12), pH 6.5,
6) Lyz+mPEG$_{20K}$-Pip-HP-ALD (12), pH 9.0,
7) Lyz+mPEG$_{20K}$-butryALD, pH 6.5,
8) Lyz+mPEG$_{20K}$-butryALD+NaCNBH$_3$, pH 6.5.
9) lysozyme (Lyz),
10) Benchmark ladder.

DETAILED DESCRIPTION OF THE INVENTION

I. Definitions

Figure 1:
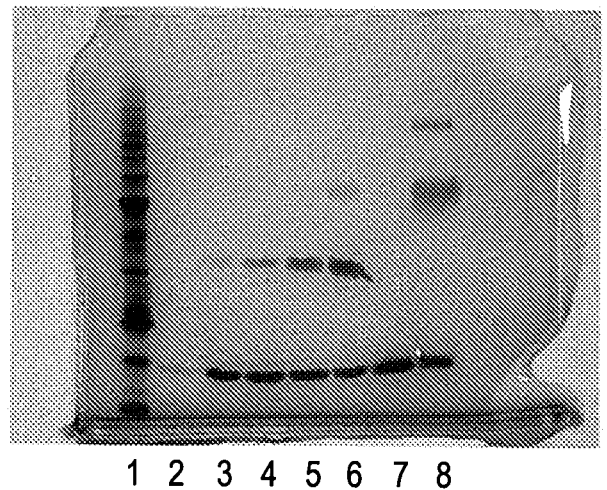
FIG. 1 shows an SDS-PAGE gel obtained from electrophoresis of reaction mixtures of conjugation reactions of a protein, lysozyme (1 mg/mL), with the polymeric reagents mPEG$_{10000}$-HP-ALD (invention compound 4) and mPEG$_{10000}$-butyrALD (prior art compound), run under different reaction conditions, as described in Example 6a.
Lane:
1) Benchmark ladder,
2) lysozyme (Lyz),
3) Lyz+mPEG$_{10K}$-HP-ALD (4), pH 6.5,
4) Lyz+mPEG$_{10K}$-HP-ALD (4), pH 7.5,
5) Lyz+mPEG$_{10K}$-HP-ALD (4), pH 9.0,
6) Lyz+mPEG$_{10K}$-HP-ALD (4), pH 7.5+NaCNBH$_3$,
7) Lyz+mPEG$_{10K}$-butyrALD (20 kD), pH 7.5,
8) Lyz+mPEG$_{10K}$-butyrALD (20 kD), pH 7.5+NaCNBH$_3$.

Before describing the present invention in detail, it is to be understood that this invention is not limited to particular polymers, synthetic techniques, active agents, and the like, as such may vary.

As used in this specification and in the claims, the singular forms "a", "an", and "the" include plural referents unless the context clearly dictates otherwise. Thus, for example, reference to "a polymer" includes a single polymer as well as two or more of the same or different polymers, reference to "a conjugate" refers to a single conjugate as well as two or more of the same or different conjugates, reference to "an excipient" includes a single excipient as well as two or more of the same or different excipients, and the like.

"Optional" and "optionally" mean that the subsequently described circumstance may or may not occur, so that the description includes instances where the circumstance occurs and instances where it does not.

In describing and claiming the present invention, the following terminology will be used in accordance with the definitions described below.

"PEG", "polyethylene glycol" and "poly(ethylene glycol)" as used herein, are meant to encompass any water-soluble poly(ethylene oxide). Typically, PEGs for use in accordance with the invention comprise the following structure "—O(CH$_2$CH$_2$O)$_m$—" where (m) is 2 to 4000. As used herein, PEG also includes "—(CH$_2$CH$_2$O)$_m$—" and "—CH$_2$CH$_2$—O(CH$_2$CH$_2$O)$_m$—CH$_2$CH$_2$—", depending upon whether or not the terminal oxygens have been displaced. When the PEG further comprises a spacer moiety (to be described in greater detail below), the atoms comprising the spacer moiety, when covalently attached to a water-soluble polymer segment, do not result in the formation of an oxygen-oxygen bond (i.e., an "—O—O—" or peroxide linkage). Throughout the specification and claims, it should be remembered that the term "PEG" includes structures having various terminal or "end capping" groups and so forth. The term "PEG" also means a polymer that contains a majority, that is to say, greater than 50%, of —CH$_2$CH$_2$O— monomeric subunits. With respect to specific forms, the PEG can take any number of a variety of molecular weights, as well as structures or geometries such as "branched," "linear," "forked," "multifunctional," "dendrimeric", and the like, to be described in greater detail below.

The terms "end-capped" or "terminally capped" are interchangeably used herein to refer to a terminal or endpoint of a polymer having an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled to can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like.

"Non-naturally occurring", with respect to a polymer or water-soluble polymer, indicates that the polymer in its entirety is not found in nature. A non-naturally occurring polymer or water-soluble polymer may, however, contain one or more subunits or portions of a subunit that are naturally occurring, so long as the overall polymer structure is not found in nature.

A "water-soluble polymer" is any polymer that is soluble in water at room temperature. Typically, a water-soluble polymer will transmit at least about 75%, more preferably at least about 95% of light, transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is still more preferred, however, that the water-soluble polymer is about 95% (by weight) soluble in water and most preferred that the water-soluble polymer is completely soluble in water.

"Molecular weight", in the context of a water-soluble polymer of the invention, such as PEG, can be expressed as either a number average molecular weight or a weight average molecular weight. Unless otherwise indicated, all references to molecular weight herein refer to the weight average molecular weight. Both molecular weight determinations, number average and weight average, can be made using gel permeation chromatography or other liquid chromatography techniques. Other methods for measuring molecular weight can also be used, such as end-group analysis or colligative properties (e.g., freezing-point depression, boiling-point elevation, or osmotic pressure) to determine number average molecular weight, or light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

An "organic radical" as used includes, for example, alkyl, substituted alkyl, alkenyl, substituted alkenyl, alkynyl, substituted alkynyl, aryl and substituted aryl.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include ethyl, propyl, butyl, pentyl, isooctyl, decyl, 3-ethyl-3-pentyl, 2-methyl-1-hexyl, and the like. As used herein, "alkyl" includes cycloalkyl, when three or more carbon atoms are referenced, and lower alkyl. "Alkylene" refers to an unsaturated bivalent radical (e.g. —$(CH_2)_n$—).

"Lower alkyl" refers to an alkyl group containing from 1 to 6 carbon atoms, preferably 1 to 4 carbon atoms, and may be straight chain or branched, as exemplified by methyl, ethyl, n-butyl, iso-butyl, and tert-butyl. When a group is defined as "alkyl" herein, lower alkyl is generally a preferred embodiment.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Alkoxy" refers to an —O—R group, wherein R is alkyl or substituted alkyl, preferably $C_1$-$C_{20}$ alkyl (e.g., methoxy, ethoxy, propyloxy, benzyl, perfluorobutyl, etc.), preferably $C_1$-$C_7$ alkyl, more preferably $C_1$-$C_7$ alkyl. "Alkoxyalkyl" refers to an —R—O—R group, where R is as defined above, and is preferably unsubstituted $C_1$-$C_7$ alkyl.

"Aminoalkyl" refers to an —NHR or —$NR_2$ group, where R is alkyl as defined above, and is preferably unsubstituted $C_1$-$C_7$ alkyl, and the two R groups in —$NR_2$ may be the same or different. The two R groups may also form a five- to seven-membered ring.

"Iminoalkyl(ene)" refers to an —R'—N=R" group, where R" represents $CH_2$, CHR, or $CR_2$, where each R is alkyl as defined above, and the two R groups in —$CR_2$ may be the same or different. R' is alkyl as defined above, i.e. an $sp^2$ hybridized carbon, or alkylene, i.e. an $sp^2$ hybridized carbon forming one member of a double bond. An R in CHR or $CR_2$ taken together with the R' may form a five- to seven-membered ring. As used herein, "alkenyl" refers to a branched or unbranched hydrocarbon group of 2 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-butynyl, isopentynyl, octynyl, decynyl, and so forth.

"Aliphatic" refers to a group containing carbon and hydrogen which is not aromatic. As used herein, it can refer to linear, branched, or cyclic groups. It can refer to saturated or unsaturated groups, with saturated groups generally being preferred.

"Aryl" means one or more aromatic rings, each of 5 or 6 core carbon atoms. Aryl includes multiple aryl rings that may be fused, as in naphthyl, or unfused, as in biphenyl. Aryl rings may also be fused or unfused with one or more cyclic hydrocarbon, heteroaryl, or heterocyclic rings. As used herein, "aryl" includes heteroaryl. An aromatic moiety (e.g., $Ar^1$, $Ar^2$, and so forth), means a structure containing aryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Non-interfering substituents" are those groups that, when present in a molecule, are typically non-reactive with other functional groups contained within the molecule. Such groups include: lower alkyl, lower alkoxy, C3-C8 cycloalkyl, e.g., cyclopropyl, cyclobutyl, and the like; halo, e.g., fluoro, chloro, bromo, and iodo; cyano; phenyl; substituted phenyl; and the like. For substitutions on a phenyl ring, the substituents may be in any orientation (i.e., ortho, meta, or para). Preferred non-interfering substituents include lower alkyl, lower alkoxy, cyclopropyl, fluoro, chloro, and cyano.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl (e.g., 0-2 substituted phenyl); substituted phenyl; and the like. "Substituted aryl" is aryl having one or more non-interfering groups as a substituent. For substitutions on a phenyl ring, the substituents may be in any orientation (i.e., ortho, meta, or para).

As used herein, the "halo" designator (e.g., fluoro, chloro, iodo, bromo, and so forth) is generally used when the halogen is attached to a molecule, while the suffix "ide" (e.g., fluoride, chloride, iodide, bromide, and so forth) is used when the halogen exists in its independent ionic form (e.g., such as when a leaving group leaves a molecule).

"Electrophile" refers to an ion or atom or collection of atoms, that may be ionic, having an electrophilic center, i.e., a center that is electron seeking, capable of reacting with a nucleophile.

"Nucleophile" refers to an ion or atom or collection of atoms that may be ionic having a nucleophilic center, i.e., a center that is seeking an electrophilic center or with an electrophile.

A basic or acidic reactant described herein includes neutral, charged, and any corresponding salt forms thereof.

As used herein, the term "ionizable hydrogen atom" ("$H_\alpha$") means a hydrogen atom that can be removed in the presence of a base, often a hydroxide or amine base. Typically, the "ionizable hydrogen atom" ("$H_\alpha$") will be a hydrogen atom attached to a carbon atom that, in turn, is attached to one or more aromatic moieties or another group or groups that in some way stabilize the carbanion that would form from loss of the ionizable hydrogen atom as a proton (or the transition state leading to said carbanion).

As used herein, the term "carboxylic acid" is a moiety having a —C(O)OH functional group, as well as moieties that are derivatives of a carboxylic acid, such derivatives including, for example, protected carboxylic acids. Thus, unless the context clearly dictates otherwise, the term carboxylic acid includes not only the acid form, but corresponding esters and protected forms as well. With regard to protecting groups suited for a carboxylic acid and any other functional group described herein, reference is made to Greene et al., "PROTECTIVE GROUPS IN ORGANIC SYNTHESIS", $3^{rd}$ Edition, John Wiley and Sons, Inc., New York, 1999.

The term "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive functional group being protected as well as the reaction conditions to be employed and the presence of additional reactive or protecting groups in the molecule, if any. Protecting groups known in the art can be found in Greene et al., supra.

As used herein, the term "functional group" or any synonym thereof is meant to encompass protected forms thereof. In particular, recitation of specific functional groups such as carboxylic acids, aldehydes, or hydroxyl groups encompasses protected forms thereof.

"Multifunctional", in the context of a polymer of the invention, means a polymer having 3 or more functional groups contained therein, where the functional groups may be the same or different. Multifunctional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer. A "difunctional" polymer means a polymer having two functional groups contained therein, either the same (i.e., homodifunctional) or different (i.e., heterodifunctional).

"Branched," in reference to the geometry or overall structure of a polymer, refers to polymer having 2 or more polymer "arms." A branched polymer may possess 2 polymer arms, 3 polymer arms, 4 polymer arms, 6 polymer arms, 8 polymer arms or more. One particular type of highly branched polymer is a dendritic polymer or dendrimer, which, for the purposes of the invention, is considered to possess a structure distinct from that of a branched polymer.

A "dendrimer" or dendritic polymer is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

In the context of the present description, the definition of a variable provided with respect to one structure or formula is applicable to the same variable repeated in a different structure, unless the context dictates otherwise. Thus, for example, the definition of "POLY," "a spacer moiety," "$R^{e1}$" and so forth with respect to a polymer can be equally applicable to a water-soluble polymer conjugate provided herein.

The terms "spacer" or "spacer moiety" (which may also be referred to as a linker or linker moiety) are used herein to refer to an atom or a collection of atoms optionally used to link one moiety to another, such as a water-soluble polymer segment to a functional moiety in a polymeric reagent. The spacer moieties of the invention are preferably hydrolytically stable but may include one or more physiologically hydrolyzable or enzymatically degradable linkages. Exemplary spacer moieties are described further below.

A "physiologically cleavable" or "hydrolyzable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, ortho esters, peptides and oligonucleotides.

A "degradable linkage" includes, but is not limited to, a physiologically cleavable bond, a hydrolyzable bond, and an enzymatically degradable linkage. Thus, a "degradable linkage" is a linkage that may undergo either hydrolysis or cleavage by some other mechanism (e.g., enzyme-catalyzed, acid-catalyzed, base-catalyzed, and so forth) under physiological conditions. For example, a "degradable linkage" can involve an elimination reaction that has a base abstraction of a proton, (e.g., an ionizable hydrogen atom, $H_\alpha$), as the driving force.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes (carbamates), and the like. Generally, a hydrolytically stable linkage is one that exhibits a rate of hydrolysis of less than about 1-2% per day under physiological conditions. Hydrolysis rates of representative chemical bonds can be found in most standard chemistry textbooks. It must be pointed out that some linkages can be hydrolytically stable or hydrolyzable, depending upon (for example) adjacent and neighboring atoms and ambient conditions. One of ordinary skill in the art can determine whether a given linkage or bond is hydrolytically stable or hydrolyzable in a given context by, for example, placing a linkage-containing molecule of interest under conditions of interest and testing for evidence of hydrolysis (e.g., the presence and amount of two molecules resulting from the cleavage of a single molecule). Other approaches known to those of ordinary skill in the art for determining whether a given linkage or bond is hydrolytically stable or hydrolyzable can also be used.

As used herein, "drug release rate" means a rate (stated as a half-life) in which half of the total amount of polymer-active agent conjugates in a system will cleave into the active agent and a polymeric residue.

The terms "active agent," "biologically active agent" and "pharmacologically active agent" are used interchangeably herein and are defined to include any agent, drug, compound, composition of matter or mixture that provides some pharmacologic, often beneficial, effect that can be demonstrated in-vivo or in vitro. This includes foods, food supplements, nutrients, nutriceuticals, drugs, proteins, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a polymer-active agent conjugate, typically present in a pharmaceutical preparation, that is needed to provide a desired level of active agent and/or conjugate in the bloodstream or in a target tissue. The exact amount will depend upon numerous factors, e.g., the particular active agent, the components and physical characteristics of the pharmaceutical preparation, intended patient population, patient considerations, and the like, and can readily be determined by one of ordinary skill in the art, based upon the information provided herein and available in the relevant literature.

The term "patient" refers to a living organism suffering from or prone to a condition that can be prevented or treated by administration of a conjugate as provided herein, and includes both humans and animals.

II. Polymeric Reagents

A. Reactive Structural Features

Polymeric reagents of the invention include, in one aspect, α-hydroxy aldehydes or ketones having the structure I:

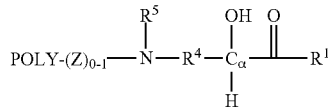

I where $R^1$ is selected from H, lower alkyl, and alkoxyalkyl, and is preferably H or methyl;

$R^4$ is a two- or three-carbon chain which may be substituted with one or more groups selected from alkyl, alkenyl, aryl, alkoxy, halo, cyano, and a water soluble polymer, wherein the carbon adjacent to Cα is not substituted with hydroxy, and wherein two substituents on $R^4$ may together form an aliphatic or aromatic ring; and $NR^5$ is a secondary or tertiary amino group which is linked to a water soluble polymer POLY, preferably a polyethylene glycol, via an optional spacer group Z, where $R^5$ is hydrogen or an alkyl group, which may form a ring with spacer group Z.

In one embodiment, $R^1$ is H, such that the reagent contains an α-hydroxy aldehyde. In further embodiments, $R^4$ is unsubstituted or is substituted with lower alkyl. $R^4$ in structure I is preferably a three-carbon chain, and may be saturated or unsaturated. More particularly, reagents in which $R^4$ is a saturated three-carbon chain may have the structure Ia:

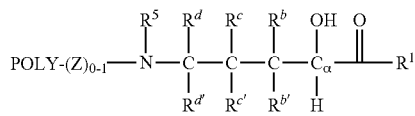

Ia where $R^1$, $NR^5$, Z and POLY are as defined above; each of the substituents Rc, $R^c$, $R^d$, and $R^{d'}$ is independently selected from hydrogen, alkyl, alkenyl, aryl, alkoxy, halo, cyano, hydroxy, and a water soluble polymer, and each of the substituents $R^b$ and $R^{b'}$ is independently selected from hydrogen, alkyl, alkenyl, aryl, alkoxy, halo, cyano, and a water soluble polymer; wherein at most one of these substituents is a water soluble polymer, and wherein any two of these substituents can together form an aliphatic ring.

In selected embodiments of this structure, the substituents $R^b$, $R^{b'}$, $R^c$, $R^{c'}$, $R^d$, and $R^{d'}$ are independently selected from hydrogen and alkyl, wherein any two such alkyl substituents, preferably on adjacent carbon atoms, can together form a 5- to 7-membered aliphatic ring.

In one embodiment, the group $R^5$ is methyl. Reagents of this class include those designated (5) and (10) herein (5-(mPEG-methyl-amino)-2-hydroxypentanal) (depicted below). In these exemplary reagents, each of $R^b$, $R^{b'}$, $R^c$, $R^{c'}$, $R^d$, and $R^{d'}$ in structure Ia is hydrogen, and Z is absent.

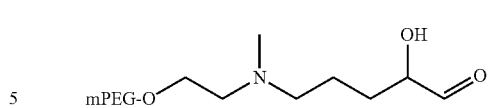

5,10

The spacer group Z, when present, preferably consists of bonds selected from alkylene, ether, thioether, amide, and amine. The spacer group, when present, is typically up to about 15 atoms in length, preferably up to 8 atoms in length. In one embodiment having a spacer group, $NR^5$ together with Z forms a ring to which POLY is linked, e.g. a piperazine ring to which POLY is linked via a ring nitrogen atom. Reagents of this class include those designated (11) and (12) herein (5-mPEG-piperazine-2-hydroxy-pentanal) (depicted below). In these exemplary reagents, each of $R^b$, $R^{b'}$, $R^c$, $R^{c'}$, $R^d$, and $R^{d'}$ in structure Ia is hydrogen.

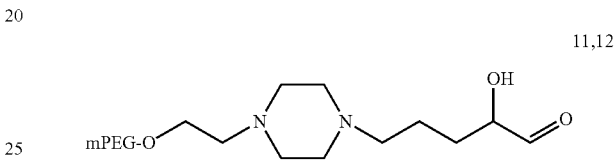

11,12

Analogous reagents include those in which the ring formed by $NR^5$ together with Z is of a different size (e.g. 5- or 7-membered rings) or composition (e.g. comprising only carbon and hydrogen in addition to nitrogen, or including other atoms such as oxygen in the ring).

In another aspect, the invention provides a polymeric α-hydroxy aldehyde or ketone reagent having the structure II:

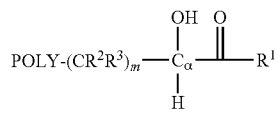

II where

POLY is a water soluble polymer, preferably a poly(ethylene glycol) (PEG), which may include a linker moiety, as described herein, linking it to $(CR^2R^3)_m$;

$R^1$ is selected from H, alkyl, hydroxyalkyl, and alkoxyalkyl;

m is 0-12, preferably 0-6; and in selected embodiments 3-6;

each $R^2$ and $R^3$ is independently selected from H, alkyl, alkylene, hydroxy, alkoxy, hydroxyalkyl, alkoxyalkyl, alkoxyalkylene, aminoalkyl, iminoalkyl, carboxylic acid, alkylcarboxylic acid, phosphate, alkylphosphate, and a further water soluble polymer, wherein at most one $R^2$ or $R^3$ groups is a water soluble polymer, and wherein two substituents $R^2$ or $R^3$ in $(CR^2R^3)_m$ can together form a ring.

In preferred embodiments, at most one group $R^2$ or $R^3$ in the polymeric reagent is selected from aminoalkyl, iminoalkyl, carboxylic acid, alkylcarboxylic acid, phosphate, and alkylphosphate. "Aminoalkyl" and "iminoalkyl" can include (cyclic amino)alkyl or (cyclic imino)alkyl; i.e. where the amine nitrogen is included in a ring, which may itself form part of the $-(CR^2R^3)_m-$ chain.

Preferably, $R^1$ is selected from H and lower alkyl; in selected embodiments, $R^1$ is H or methyl.

A polymeric reagent of structure II may be a polymeric derivative of a reducing sugar, such as ribose, xylose, arabinose, lyxose, mannose, or fructose, which are α-hydroxy aldehydes or ketones in their open ring form. Reagents based on the 3-deoxy analogs of reducing sugars, such as 3-deoxy ribose, are preferred. One such reagent is the compound designated herein as 13 (depicted below with the ribose configuration).

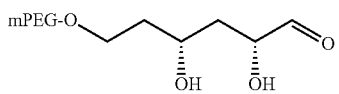

In selected embodiments, the reagents II do not include polymeric derivatives of reducing sugars which are not 3-deoxy analogs. That is, in preferred embodiments, the substituents $R^2$ and $R^3$ on the carbon adjacent to Cα do not include a 1,2,3-trihydroxypropyl group; nor does —(CR²R³)$_m$— include a backbone 1,2,3-trihydroxypropyl residue adjacent to Cα. More particularly, the reagents do not include polymeric derivatives of D-glucose or D-galactose, in particular the 3- or 6-ethers of D-glucose or D-galactose with PEG. Such reagents tend to produce conjugates which are less stable than those produced by the 3-deoxy analogs, due to the presence of the 3-hydroxyl group adjacent a carbonyl group in the conjugate.

In still further embodiments, —(CR²R³)$_m$— in structure II is defined by —CH₂—CHR$^x$—C(NH₂)R$^y$—, where R$^x$ and R$^y$ form a 5- to 7-membered aliphatic ring to which POLY is linked. Such reagents include those illustrated as follows, where n is 0 to 2:

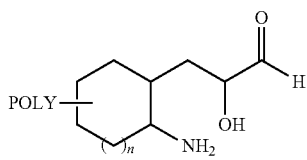

Also provided are polymeric reagents having the structure III:

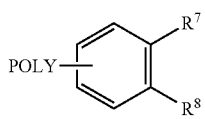

where

POLY is a water soluble polymer, such as a polyethylene glycol, which may include a linker moiety, as described herein, linking it to the aromatic ring; and (i) $R^7$ is —CH(OH)—C(=O)—R¹, and $R^8$ is selected from —C(=O)OH, —CH₂OH, —C(=O)N(R¹)₂, —CH₂N(R¹)₂, —OH, and —N(R¹)₂, and is preferably selected from —C(=O)OH, —CH₂OH, —C(=O)N(R¹)₂, and —CH₂N(R¹)₂; or (ii) $R^7$ is —CHR¹CH(OH)—C(=O)—R¹, and $R^8$ is —OH or —N(R¹)₂;

where each R¹ is independently selected from H, lower alkyl, and alkoxyalkyl, and is preferably independently selected from H and methyl. In selected embodiments, R¹ attached to C(=O) is H, such that the reagent contains an α-hydroxy aldehyde. In other embodiments, each R¹ is H.

Exemplary reagents of this class include the compounds designated herein as 6, where $R^7$ is —CH(OH)—C(=O)—H and $R^8$ is —C(=O)OH; 7, where $R^7$ is —CH(OH)—C(=O)—H and $R^8$ is —OH; and 8, where $R^7$ is —CH₂CH(OH)—C(=O)—H and $R^8$ is —OH (shown below in protected form, with attached mPEG polymers). Analogous reagents include those in which the phenolic hydroxy group (OH) is replaced by NH₂ or N(CH₃)₂ (that is, $R^8$ is —NH₂ or —N(CH₃)₂).

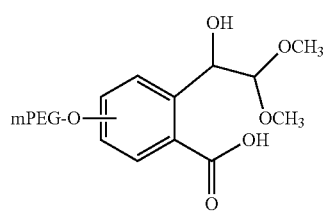

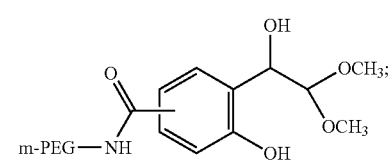

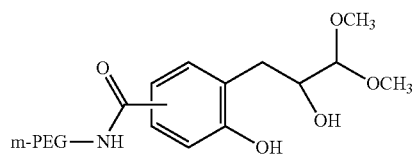

As noted above, the POLY component of all the disclosed reagents is a water soluble polymer, preferably a poly(ethylene glycol). The POLY component of the reagent, and of the resulting conjugates, is discussed in further detail below. The reagents typically have from one to three attached polymers per molecule, and more typically one or two. In one embodiment, a reagent has one attached polymer per molecule.

It should be noted that the invention encompasses protected (typically acetal and ketal) forms of the aldehyde and ketone in the structures represented herein; for example, C=O can be replaced by C(OR)₂, where R is alkyl, and the two R groups constitute two monovalent alkyl groups or one bivalent alkyl group (i.e. a cyclic protecting group).

B. Reactivity and Self-Catalysis

The polymeric α-hydroxy aldehyde or α-hydroxy ketone reagents described herein can be conjugated to compounds containing a reactive amine group to form a stable conjugate. The reaction takes place in a single step; that is, no reductive step is needed to convert the initial product to a stable derivative, as in the widely employed reductive amination of aldehydes and ketones.

In reactions of the current reagents with amine-containing compounds, the initial conjugation product undergoes an acid- or base-catalyzed rearrangement to an aminoketone, as shown in the second step below. A version of this rearrangement was first reported by Amadori, in the conversion of N-glycosides of aldoses to N-glycosides of the corresponding ketoses.

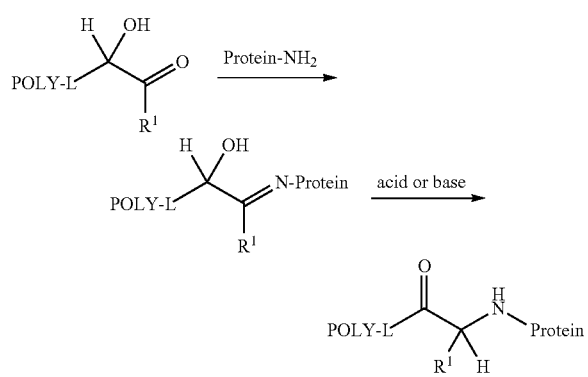

The rearrangement step which immediately follows conjugation using the current reagents is acid- or base-catalyzed, as noted above. Accordingly, the reaction is preferably carried out in the presence of anionic buffer salts, such as carbonate and phosphate.

In one embodiment, the polymeric reagent itself incorporates an internal proton-abstracting (basic) functional group, to promote more efficient rearrangement of the imine intermediate. Substituents that provide this functional group may include carboxylates (e.g. aspartic acid derivatives), phosphates, hydroxyl groups, and amines or imines, cyclic as well as acyclic. The substituent is appropriately situated, via a linker if necessary, to position the group for proton abstraction, preferably providing a 4- or 5-bond spacing between the abstracting atom and the hydrogen atom on the α-carbon (that is, a 3- or 4-bond spacing between the abstracting atom and the α-carbon itself).

The self-catalysis mechanism is illustrated below, showing the preferred 5-bond spacing, such that the transition state represents a 6-membered ring. The proton-abstracting atom is represented by X in this structure.

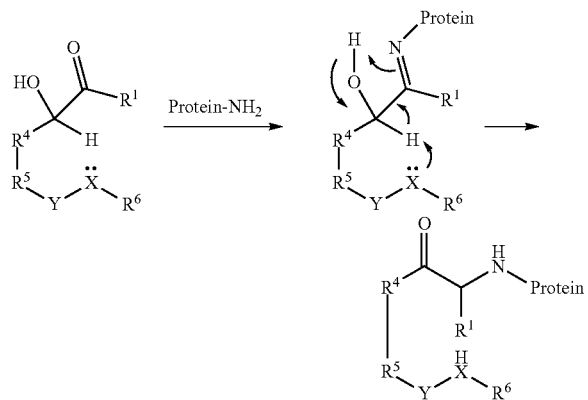

Preferred self-catalyzing reagents include reagents of structures I/Ia and III above, as well as reagents of structure II above in which one group $R^2$ or $R^3$ is selected from hydroxy, alkoxy, hydroxyalkyl, alkoxyalkyl, alkoxyalkylene, amino, aminoalkyl, iminoalkyl, carboxylic acid, alkylcarboxylic acid, phosphate, and alkylphosphate; and the group $R^2$ or $R^3$ and the value of m are selected such that an oxygen or nitrogen atom on $R^2$ or $R^3$ is separated from Cα by a four-bond path (or, less preferably, a three-bond path). Preferably, in such reagents, one group $R^2$ or $R^3$ is selected from amino, aminoalkyl, iminoalkyl, carboxylic acid, and alkylcarboxylic acid.

Self-catalyzing reagents can also be represented by structure VII below:

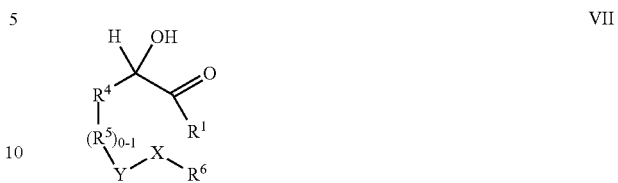

where:

$R^1$ is selected from H, lower alkyl, and alkoxyalkyl;

$R^4$ and $R^5$ are carbon atoms, each of which is substituted with two groups selected from hydrogen, alkyl, alkenyl, alkoxy, a non-interfering substituent as defined herein (e.g. halo, cyano, aryl or substituted aryl), and a water soluble polymer; Y is carbon, X is nitrogen or oxygen, and $R^6$ is selected from an electron pair, hydrogen, alkyl, alkenyl, alkoxy, and a water soluble polymer; such that (a) Y—X—$R^6$ represents a carboxyl, alkoxylalkyl, aminoalkyl, or iminoalkyl(ene) moiety, where Y—X may be part of a cyclic structure in the case of aminoalkyl or iminoalkyl(ene), or (b) X—$R^6$ taken alone represents amino or hydroxyl;

wherein $R^4$ and $R^5$ taken together, or $R^5$ and Y taken together, or $R^4$ and Y taken together when $R^5$ is absent, may form one side of a five- or six-membered ring which may be substituted with a water soluble polymer;

and wherein the reagent comprises at least one water soluble polymer, and typically comprises at most one or two water soluble polymers.

Preferred structures where $R^5$ is present (subscript=1) provide a six-membered transition state for the rearrangement, as illustrated above. Structures in which $R^5$ is absent (subscript=0) provide a five-membered transition state for the rearrangement and can also be useful.

Preferably, $R^1$ is selected from H and lower alkyl; in selected embodiments, $R^1$ is H or methyl. When $R^4$ and $R^5$, or $R^5$ and Y, form one side of a five- or six-membered ring, such a ring may be further substituted with one or more non-interfering substituents as defined above.

In one embodiment, Y—X in structure VII represents aminoalkyl, and has the structure —CH$_2$—NR—, where R is lower alkyl. A reagent of this type in which $R^6$ is PEG, R is methyl, and each of $R^4$ and $R^5$ is —CH$_2$— is designated herein as PEG-MAHP-ALD (5 or 10) (where MAHP indicates methylamino 2-hydroxy pentanal) and is used in the working Examples below. This reagent is also an embodiment of structure I/Ia, as noted above.

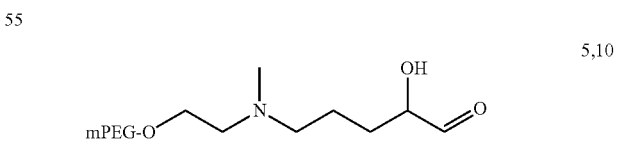

In another embodiment, Y—X in structure VII represents a carboxyl group (—C(═O)—O—) and $R^6$ is hydrogen, giving a carboxylic acid (COOH)-substituted reagent. A reagent of this type in which $R^1$ is hydrogen, and $R^4$ and $R^5$ form one side of a benzene ring which is substituted with mPEG is shown (in aldehyde-protected form) below:

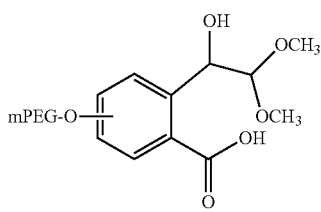

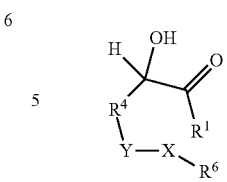

This reagent is also an embodiment of structure III, as noted above.

In a further embodiment, in which Y—X—$R^6$ represents an iminoalkyl(ene) moiety, Y—X in structure VII represents a 4-imidazoyl group (an embodiment of a cyclic imino group). A reagent of this type in which $R^4$ is substituted with hydrogen and —Z-PEG, where Z is an amide linker, and $R^5$ is —$CH_2$—, is shown below. (Preparation is described in Example 3.) This reagent is also an embodiment of structure II above, where $R^2$ or $R^3$ is (cyclic imino)alkyl.

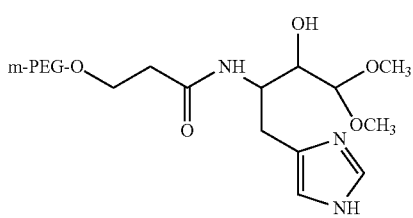

In a further embodiment, X—$R^6$ taken alone represents a hydroxyl group, and $R^5$ and Y taken together form one side of a six-membered ring, such as a benzene ring, which is substituted with a water soluble polymer. A reagent of this type, where $R^4$ is —$CH_2$—, is shown (in protected form) on the right below (structure 8).

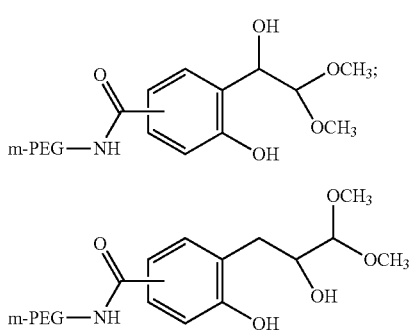

As noted above, the reagents of structure VII where $R^5$ is present (subscript=1) are designed to provide a favorable six-membered transition state for the rearrangement. Also useful are structures designed to provide a five-membered transition state; these would essentially have the structure VII with $R^5$ omitted (subscript=0), so that $R^4$ is directly connected to Y, as shown below (structure VII'). In this case, as noted above, $R^4$ and Y taken together may form one side of a five- or six-membered ring which may be substituted with a water soluble polymer. An example of this class of reagent is shown (in protected form) in the structure on the left above (structure 7).

Reagents 7 and 8 are also embodiments of structure III, as noted above.

The polymeric reagents are prepared according to standard synthetic methods available to those skilled in the art. For example, a precursor compound having a protected aldehyde or ketone at one terminus and a reactive group at another terminus is reacted with a polymer having a complementary reactive group. Alternatively, the aldehyde or ketone may be generated following attachment of the polymer to a suitable precursor molecule. See, for example, the schemes illustrated in Examples 1-5, 7-10 and 18-19 below, which are not to be regarded as limiting.

C. The Water Soluble Polymer

With respect to a given water-soluble polymer in the presently described polymeric reagents, each water-soluble polymer (e.g., $POLY^1$, $POLY^2$ etc.) can comprise any polymer so long as the polymer is water-soluble. Moreover, a water-soluble polymer as used herein is typically non-peptidic.

Although preferably a poly(ethylene glycol), a water-soluble polymer for use herein can be, for example, other water-soluble polymers such as other poly(alkylene glycols), such as poly(propylene glycol) ("PPG"), copolymers of ethylene glycol and propylene glycol and the like, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), such as described in U.S. Pat. No. 5,629,384. The water soluble polymer can be a homopolymer, copolymer, terpolymer, nonrandom block, and random block polymer of any of the foregoing.

Thus, the water soluble polymer preferably comprises up to three different monomers selected from the group consisting of: alkylene glycol, such as ethylene glycol or propylene glycol; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; saccharide; α-hydroxy acid, such as lactic acid or glycolic acid; phosphazene, oxazoline, and N-acryloylmorpholine. Preferred monomer types include alkylene glycol, olefinic alcohol, hydroxyalkyl methacrylamide or methacrylate, N-acryloylmorpholine, and α-hydroxy acid.

Preferably, the polymer is a copolymer of two monomers selected from this group, or, more preferably, a homopolymer of one monomer selected from this group. Thus, representative POLYs include poly(alkylene glycols) such as poly(ethylene glycol), poly(propylene glycol) ("PPG"), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, and poly(N-acryloylmorpholine). POLY can be a homopolymer, an alternating copolymer, a random copolymer, a block copolymer, an alternating tripolymer, a random tripolymer, or a block tripolymer of any of the above. The two monomers in a copolymer may be of the same monomer type, for example, two alkylene glycols, such as ethylene glycol and propylene glycol.

In instances where the polymeric reagent comprises two or more water-soluble polymers, each water-soluble polymer in the overall structure can be the same or different. It is preferred, however, that all water-soluble polymers in the overall structure are of the same type. For example, it is preferred that all water-soluble polymers within a given structure are each a poly(ethylene glycol).

Any water-soluble polymer having at least one reactive terminus can be used to prepare a polymeric reagent in accordance with the invention. Although water-soluble polymers bearing only a single reactive terminus can be used, polymers bearing two, three, four, five, six, seven, eight, nine, ten, eleven, twelve or more reactive termini suitable for conversion as set forth herein can be used. In the context of being present within an overall structure, a water-soluble polymer has from 1 to about 300 termini.

The polymer component can have any of a number of different geometries; for example, POLY can be linear, branched, or forked, as will be described in further detail below. Most typically, POLY is linear or is branched, for example, having 2 polymer arms.

Although the weight average molecular weight of any individual water-soluble polymer can vary, the weight average molecular weight of any given water-soluble polymer will typically be in the following range: 100 Daltons to about 150,000 Daltons. Exemplary ranges, however, include weight-average molecular weights in the range of about 880 Daltons to about 5,000 Daltons, in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, in the range of about 880 Daltons to about 60,000 Daltons, in the range of about 440 Daltons to about 40,000 Daltons, in the range of about 440 Daltons to about 30,000 Daltons, and in the range of from about 40,000 Daltons to about 120,000 Daltons. For any given water-soluble polymer, PEGs having a molecular weight in one or more of these ranges are preferred.

Exemplary weight-average molecular weights for the water-soluble polymer include about 100 Daltons, about 200 Daltons, about 300 Daltons, about 400 Daltons, about 440 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 16,000 Daltons, about 17,000 Daltons, about 18,000 Daltons, about 19,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total weight average molecular weight of any of the foregoing can also be used.

When a PEG is used as the water-soluble polymer in the polymeric reagent, the PEG typically comprises a number of ($OCH_2CH_2$) monomers (or ($CH_2CH_2O$) monomers, depending on how the PEG is defined). As used throughout the description, the number of repeating units is identified by the subscript "n" in "($OCH_2CH_2$)$_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

Each water-soluble polymer is typically biocompatible and non-immunogenic. With respect to biocompatibility, a substance is considered biocompatible if the beneficial effects associated with use of the substance alone or with another substance (e.g., an active agent) in connection with living tissues (e.g., administration to a patient) outweighs any deleterious effects as evaluated by a clinician, e.g., a physician. With respect to non-immunogenicity, a substance is considered non-immunogenic if use of the substance alone or with another substance in connection with living tissues does not produce an immune response (e.g., the formation of antibodies) or, if an immune response is produced, that such a response is not deemed clinically significant or important as evaluated by a clinician. It is particularly preferred that the polymers and water-soluble polymer segments, described herein as well as conjugates of active agents and the polymers are biocompatible and non-immunogenic.

In preferred embodiments, POLY is a poly(ethylene glycol). PEG polymers are typically clear, colorless, odorless, soluble in water, stable to heat, inert to many chemical agents, and non-toxic, and do not hydrolyze or deteriorate (unless specifically designed to do so). Poly(ethylene glycol) is highly biocompatible and substantially non-immunogenic. When conjugated to a pharmacologically active agent, the PEG molecule tends to mask the agent and can reduce or eliminate any immune response to the agent. PEG conjugates tend not to produce a substantial immune response or cause clotting or other undesirable effects.

The molecular weight of the PEG component may vary, as described above, but preferred polymers include from about 3 to about 4,000, or from about 3 to about 3,000, or more preferably from about 20 to about 1,000 monomeric units.

In one form, free or nonbound PEG is a linear polymer terminated at each end with hydroxyl groups:

HO—$CH_2CH_2$O—($CH_2CH_2$O)$_{m'}$—$CH_2CH_2$—OH wherein (m') typically ranges from zero to about 4,000, preferably from about 20 to about 1,000.

The above polymer, alpha-,omega-dihydroxylpoly(ethylene glycol), can be represented in brief form as HO-PEG-OH, where it is understood that the -PEG- symbol can represent the following structural unit:

—$CH_2CH_2$O—($CH_2CH_2$O)$_{m'}$—$CH_2CH_2$— where (m') is as defined as above.

An end-capped PEG, where PEG is terminally capped with an inert end-capping group, is preferred for preparing the reagents of the invention. Preferred end-capping moieties include alkoxy, substituted alkoxy, alkenyloxy, substituted alkenyloxy, alkynyloxy, substituted alkynyloxy, aryloxy, and substituted aryloxy. Most preferred end-capping groups are methoxy, ethoxy, and benzyloxy. The structure of mPEG (methoxy-PEG-OH) is given below:

where (m') is as described above.

The capping group may also be a phospholipid. A preferred phospholipid is a dialkyl phosphatidylethanolamine, such as distearoyl phosphatidylethanolamine (DSPE; see structure below). Other suitable phospholipids include, for example, phosphatidyl serines, phosphatidyl glycerols, phosphatidyl inositols, and phosphatidyl cholines, all of which are well known in the art and available commercially. A reactive group on the phosphate head group can be used to link the lipid to a PEG chain; for example, the terminal amine in DSPE can be linked to PEG via a carbamate linkage.

Multi-armed or branched PEG molecules, such as those described in U.S. Pat. No. 5,932,462, can also be used as the PEG polymer. For example, PEG can have the structure:

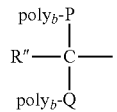

wherein:
poly$_a$ and poly$_b$ are PEG backbones (either the same or different), such as methoxy poly(ethylene glycol);
R" is a nonreactive moiety, such as H, methyl or a PEG backbone; and
P and Q are nonreactive linkages.

In a preferred embodiment, the branched PEG polymer is methoxy poly(ethylene glycol) disubstituted lysine. Invention compound 14 is another example of a reagent utilizing a branched PEG.

In addition, the PEG can comprise a forked PEG. An example of a free or nonbound forked PEG is represented by the following structure:

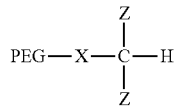

where X is a spacer moiety and each Z is an activated terminal group linked to CH by a chain of atoms of defined length. International Application Pubn. No. WO 99/45964 discloses various forked PEG structures capable of use in the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, each water-soluble polymer in the polymeric reagent can also be prepared with one or more weak or degradable linkages in the polymer, including any of the above described polymers. For example, PEG can be prepared with ester linkages in the polymer that are subject to hydrolysis. As shown below, this hydrolysis results in cleavage of the polymer into fragments of lower molecular weight:

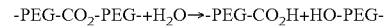

Other hydrolytically degradable linkages, useful as a degradable linkage within a polymer backbone, include carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

It is understood by those of ordinary skill in the art that the term poly(ethylene glycol) or PEG represents or includes all the above forms of PEG.

Those of ordinary skill in the art will recognize that the foregoing discussion concerning substantially water-soluble polymers is by no means exhaustive and is merely illustrative, and that all polymeric materials having the qualities described above are contemplated. As used herein, the term "water-soluble polymer" refers both to a molecule as well as the residue of water-soluble polymer that has been attached to another moiety.

D. Linker Moieties

A linker moiety, or simply "linker", may be used to connect polymer segments making up the component POLY to each other, or to connect the polymer component POLY to the functional portion of the reagent. The term POLY as used herein is understood to optionally include such a linker. A linker may be a single atom, such as an oxygen or a sulfur, two atoms, or a number of atoms. A linker is typically but is not necessarily linear in nature. The overall length of the linker will typically range between 1 to about 40 atoms, where by length is meant the number of atoms in a single chain, not counting substituents. For instance, —$CH_2$— counts as one atom with respect to overall linker length, and —$CH_2CH(CH_3)O$— counts as 3 atoms in length. Preferably, a linker will have a length of about 1 to about 20 atoms, or, more preferably, from about 2 to about 15 atoms.

A linker can be a single functional group such as an amide, an ester, a urethane (carbamate), or a urea, or it may contain methylene or other alkylene groups flanking either side of the single functional group. Alternatively, a linker may contain a combination of functional groups, which can be the same or different. A linker can be an alkylene chain, optionally containing one or more oxygen or sulfur atoms (i.e., an ether or thioether linkage). Also included are alkylene chains containing a nitrogen atom (i.e. an amine linkage.) Preferred linkers are those that are hydrolytically stable.

Illustrative linkers are those corresponding to either of the following structures:

—(CH$_2$)$_c$-D$_e$-(CH$_2$)$_f$—  or  —(CH$_2$)$_p$-M$_r$-C(O)—K$_s$-(CH$_2$)$_q$—. In referring to these structures, the variable "c" ranges from zero to 8; "D" is Q, NH, or S; the variable "e" is 0 or 1; the variable "f" ranges from zero to 8; the variable "p" ranges from zero to 8; "M" is —NH or O; "K" is NH or O; the variable "q" ranges from zero to 8, and the variables "r" and "s" are each independently 0 or 1.

Exemplary linker moieties include, but are not limited to, the following: —O—, —S—, —C(O)—, —S(O$_2$)—, —S(O)—, —NH—S(O$_2$)—, —S(O$_2$)—NH—, —CH═CH—, —O—CH═CH—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —S—CH$_2$—, —CH$_2$—S—, —S—CH$_2$—CH$_2$—, —CH$_2$—S—CH$_2$—, —CH$_2$—CH$_2$—S—, —S—CH$_2$—CH$_2$—CH$_2$—, —CH$_2$—S—CH$_2$—CH$_2$—, —CH$_2$—CH$_2$—S—CH$_2$—, —CH$_2$—CH$_2$—CH$_2$—S—, —S—CH$_2$—CH$_2$—CH$_2$—CH$_2$—, —CH$_2$—S—CH$_2$—CH$_2$—CH$_2$—, —CH$_2$—CH$_2$—S—CH$_2$—CH$_2$—, —CH$_2$—CH$_2$—CH$_2$—S—CH$_2$—, —CH$_2$—CH$_2$—CH$_2$—CH$_2$—S—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—C(O)—NH—, —NH—C(O)—CH$_2$—CH$_2$—C(O)—NH—, —NH—C(O)—CH$_2$—CH$_2$—CH$_2$—C(O)—NH—, —NH—C(O)—CH$_2$—CH$_2$—CH$_2$—CH$_2$—C(O)—NH—, —NH—C(O)—CH═CH—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—, —CH$_2$—CH$_2$—C(O)—NH—CH$_2$—CH$_2$—NH—C(O)—CH$_2$—, —CH$_2$—CH$_2$—C(O)—NH—CH$_2$—CH$_2$—NH—C(O)—CH$_2$—CH$_2$—, bivalent cycloalkyl, and amino acids.

Also included are —N(R$^6$)—, where R$^6$ is H or an organic radical selected from the group consisting of alkyl, substituted alkyl, alkenyl, substituted alkenyl, alkynyl, substituted alkynyl, aryl and substituted aryl; and —NH—C(O)—O—(CH$_2$)$_h$—(OCH$_2$CH$_2$V or —O—C(O)—NH—(CH$_2$)$_h$—(OCH$_2$CH$_2$)$_j$—, where (h) is zero to six, and (j) is zero to 20.

Other specific spacer moieties have the following structures: —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylenes contained in the structure, e.g., (CH$_2$)$_{1-6}$ means that the structure can contain 1, 2, 3, 4, 5 or 6 methylenes.

A linker may include combinations of two or more of any of the foregoing.

Additionally, any of the above spacer moieties may further include an ethylene oxide oligomer chain comprising 1 to 20 ethylene oxide monomer units (i.e., —(CH$_2$CH$_2$O)$_{1-20}$). That is, the ethylene oxide oligomer chain can occur before or after the spacer moiety, and optionally in between any two atoms of a spacer moiety comprised of two or more atoms. However, the oligomer chain would not be considered part of the spacer moiety if the oligomer is adjacent to a polymer segment and merely represents an extension of the polymer segment. For example, where POLY is defined as CH$_3$—O—(CH$_2$CH$_2$O)$_n$—, —CH$_2$CH$_2$O— would not be a linker moiety, since such a definition would merely represent an extension of the polymer. However, a linker could contain one or more —CH$_2$CH$_2$O— subunits flanked by one or a combination of illustrative linkers as provided above.

Preferably, the linker is hydrolytically stable, and may contain one or more of the following functional groups: amide, urethane, ether, thioether, or urea. However, hydrolytically degradable linkages, such as carboxylate ester, phosphate ester, orthoester, anhydride, imine, acetal, ketal, oligonucleotide, or peptide, may also be present.

III. Conjugation Method

In accordance with the invention, methods of forming stable conjugates of water-soluble polymers with amine-containing biologically active molecules are provided. As noted above, the reaction takes place in a single step; that is, no reductive step is needed to convert the initial product to a stable derivative, as in the widely employed reductive amination of aldehydes and ketones.

Accordingly, the invention provides a method of conjugating a water soluble polymer with a compound having a reactive amine group, the method comprising: reacting the compound with a polymeric reagent comprising an α-hydroxy aldehyde or a terminal α-hydroxy ketone, respectively, linked to a water soluble polymer, thereby forming a conjugate in which the water soluble polymer is linked to a moiety having the structure —C(═O)—CHR$^1$—NH—B, where R$^1$ is hydrogen or methyl, respectively, and NH—B represents the residue of the amine-containing compound.

In preferred embodiments, the polymeric reagent further comprises a proton-abstracting functional group containing a proton-abstracting atom selected from oxygen and nitrogen, situated such there is a 3- or 4-bond spacing, preferably a 4-bond spacing, between the proton-abstracting atom and the α-carbon of the α-hydroxy aldehyde or α-hydroxy ketone. Such reagents are able to undergo a "self-catalyzed" conjugation reaction, as described above.

More particularly, the invention provides a method of conjugating a water soluble polymer with a compound having a reactive amine group, by reacting the amine-containing compound with a polymeric reagent having the structure I/Ia, II or III as shown herein, where the reagent comprises at least one water soluble polymer; to form a conjugate having structure IV, V or VI as described herein, respectively, wherein —NH—B in structure IV,V or VI represents the residue of the amine-containing compound.

The conjugation method may employ a polymeric derivative of a reducing sugar, such as ribose, xylose, arabinose, lyxose, galactose, glucose, mannose, and fructose, which are α-hydroxy aldehydes or ketones in their open ring form. Reagents based on the 3-deoxy analogs of reducing sugars, such as 3-deoxy ribose, are preferred. Such reagents are advantageous over the corresponding derivatives of the native sugars, because the absence of the 3-hydroxyl group in the eventual conjugated product reduces opportunities for degradation of the conjugated product.

In general, preferred embodiments of the method employ preferred embodiments of the reagents as described herein. The amine-containing compound is typically a biologically active or biologically relevant compound, as described further below.

A. Reaction Conditions

Suitable solvents for carrying out the conjugation reaction include buffers such as aqueous sodium phosphate, sodium acetate, sodium carbonate, phosphate buffered saline (PBS), sodium borate, and N-(2-hydroxyethyl)piperazine-N'-(2-ethanesulfonic acid) (HEPES). For conjugation to a protein, the polymeric reagent is typically added to the protein-containing solution at an equimolar amount or at a molar excess relative to target protein. Molar excesses of PEG-reagent relative to target protein are typically in the range of about 2 to 5. The conjugation reaction is typically carried out at temperatures at or below about room temperature (25° C.), although temperatures may range from about −15° C. to about 100° C., more preferably from about 4° C. to 37° C., for approximately one to 24 hours. Exemplary conjugation reaction conditions are described in Examples 6 and 11-13 below.

Conditions for conjugation to a small molecule, e.g. amphotericin B or other amine-containing molecules as discussed below, will vary according to the small molecule being modified. Typically, however, the conjugation is conducted using a slight molar excess of polymeric reagent relative to small molecule, e.g., about 1.2-1.5, to about a 5 to 10-fold molar excess. In some instances, depending upon the molecule, the small molecule drug may actually be used in excess, such as when the PEG-small molecule conjugate precipitates in the reaction solvent, e.g., ether, while the unreacted drug remains in solution.

The exact reaction time is determined by monitoring the progress of the reaction over time. Progress of the reaction is typically monitored by withdrawing aliquots from the reaction mixture at various time points and analyzing the reaction mixture by SDS-PAGE or MALDI-TOF mass spectrometry or any other suitable analytical method.

B. Characterization and Optional Separation of PEG-mers

Optionally, conjugates produced by reacting a PEGylated reagent of the invention with a biologically active agent are purified to obtain/isolate different PEGylated species, when the conjugated molecule (e.g., a protein) and reaction conditions are such that multiple PEGylated species are to be expected. For reaction of proteins with lower molecular weight PEGs, e.g., having molecular weights less than about 20 kilodaltons, the reaction product can be purified to obtain a distribution around a certain number of PEGs per protein molecule. For example, the product mixture can be purified to obtain an average of anywhere from one to five PEGs per protein, typically an average of about 3 PEGs per protein. The strategy for purification of the final conjugate reaction mixture will depend upon a number of factors, such as the molecular weight of the polymer employed, the particular protein, and the residual activity and in vivo properties of the individual conjugate species.

PEG conjugates having different molecular weights can be isolated using gel filtration chromatography. For example, in an exemplary reaction where a PEG reagent having a molecular weight of about 20 kDa is randomly conjugated to a 100 kDa protein, the resulting reaction mixture will likely contain unmodified protein (MW 100 kDa), mono-pegylated protein (MW 120 kDa), di-pegylated protein (MW 140 kDa), etc. Gel filtration columns suitable for carrying out this type of separation include Superdex® and Sephadex® columns available from Amersham Biosciences. Selection of a particular column will depend upon the desired fractionation range desired. Elution is generally carried out using a non-amine based buffer, such as phosphate, acetate, or the like. The collected fractions may be analyzed by a number of different methods, for example, (i) OD at 280 nm for protein content, (ii) BSA protein analysis, (iii) iodine testing for PEG content, or (iv) by running an SDS PAGE gel, followed by staining with barium iodide.

Separation of positional isomers (i.e. conjugates having PEG attached to different locations on a protein), generally not achievable by molecular weight-based methods, can be carried out by reverse phase chromatography using e.g. an RP-HPLC C18 column (Amersham Biosciences or Vydac).

C. Conjugation to Proteins: Random and N-Terminal Selective

Generally, the polymeric reagents of the invention can be used to selectively target the modification of the N-terminus of a protein, under conditions that differentiate the reactivity of the α-amine at the N-terminal amino acid. Reaction conditions for preparing an N-terminally modified protein or peptide include (i) dissolving the protein or peptide to be modified in a non-amine-containing buffer (e.g., at a pH range from about 4 to about 6.5, preferably from about 5 to 6.5, most preferably at a pH of about 5 to 5.5), (ii) adding to the protein or peptide solution a polymeric reagent (α-hydroxy aldehyde or ketone) of the invention, and (iii) allowing the protein or peptide and polymeric reagent to react to form the conjugate.

Reaction under conditions of higher pH can be used for random attachment of a polymeric reagent (α-hydroxy aldehyde or ketone). More specifically, to covalently attach a polymeric reagent to any number of lysine residues that are surface accessible, a protein or peptide (such as those exemplary biomolecules provided below) is typically reacted with a polymeric reagent of the invention in a non amine-containing buffer at mild pH, generally ranging from about 5 to 8, more preferably from about 6.5 to 8. Non-amine containing buffers are preferred, since the amino-groups in the buffer can compete with protein amino groups for coupling to the polymeric reagent. A suitable non-amine containing buffer is selected having an appropriate pK for the desired pH range for conducting the conjugation chemistry. The coupling reaction generally takes anywhere from minutes to several hours (e.g., from 5 minutes to 24 hours or more), and on average, coupling is achieved between about 0.2 and 4 hours.

The degree of modification, that is, the number of PEGs that are covalently attached at available sites on the target molecule, can be increased by increasing, either independently or simultaneously, any one or more of: molar ratio of polymeric reagent to protein or peptide, temperature, reaction time, and pH.

IV. Polymeric Conjugates

As described above, the present invention provides polymeric reagents useful in providing conjugates having a degradable linkage between a polymer and another moiety. Without wishing to be bound by theory, it is believed that the conjugates degrade in such as way as to minimize or eliminate entirely any residue or "tag" of the polymeric reagent used to form the conjugate. As a consequence, it is possible, upon hydrolysis of a conjugate formed from the reaction of a polymeric reagent described herein with an amine-containing active agent, to regenerate or recover the original unconjugated and unmodified form of the active agent.

In accordance with the invention, polymeric conjugates, comprising a water soluble polymer covalently linked to a biologically active molecule via an α-amino ketone linkage, are provided. The conjugates are prepared by reaction of a reagent of structure I/Ia, II or III herein with an amine-containing compound.

In accordance with reagents having the structure I/Ia above, such conjugates may have the structure IV:

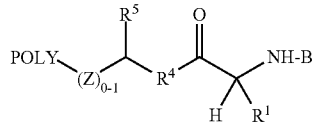

IV where $R^1$ is selected from H, lower alkyl, and alkoxyalkyl, and is preferably H or methyl;

$R^4$ is a two- or three-carbon chain which may be substituted with one or more groups selected from alkyl, alkenyl, aryl, alkoxy, halo, cyano, and a water soluble polymer; wherein the carbon adjacent to the carbonyl carbon is not substituted with hydroxyl, and wherein two substituents on $R^4$ may form an aliphatic or aromatic ring;

$NR^5$ is a secondary or tertiary amino group which is linked to a water soluble polymer POLY, such as a polyethylene glycol, via an optional spacer group Z, where $R^5$ is hydrogen or an alkyl group, which may form a ring with spacer group Z; and —NH—B represents the residue of an amine-containing biologically active compound.

In accordance with reagents having the structure II above, such conjugates may also have the structure V:

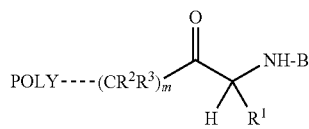

V wherein:

POLY is a water soluble polymer, preferably a PEG, which may include a linker moiety, as described herein, linking it to $(CR^2R^3)_m$;

$R^1$ is selected from H, alkyl, hydroxyalkyl, and alkoxyalkyl, and preferably from H and methyl;

m is 0-12, preferably 0-6, and in selected embodiments 3-6; and each $R^2$ and $R^3$ is independently selected from H, alkyl, alkylene, hydroxy, amino, alkoxy, hydroxyalkyl, alkoxyalkyl, alkoxyalkylene, aminoalkyl, iminoalkyl, carboxylic acid, alkylcarboxylic acid, phosphate, alkylphosphate, and a further water soluble polymer, wherein at most one $R^2$ or $R^3$ group is a water soluble polymer, and wherein two substituents $R^2$ or $R^3$ on $(CR^2R^3)_m$ may form a ring, preferably an aliphatic ring; and —NH—B represents the residue of an amine-containing biologically active compound.

In preferred embodiments, at most one group $R^2$ or $R^3$ is selected from aminoalkyl, iminoalkyl, carboxylic acid, alkylcarboxylic acid, phosphate, and alkylphosphate. As noted above, aminoalkyl and iminoalkyl can include (cyclic amino)alkyl or (cyclic imino)alkyl; i.e. where the amine nitrogen is included in a ring, which may itself form part of the $—(CR^2R^3)_m—$ chain.

Further conjugates of the invention include those of structure VI:

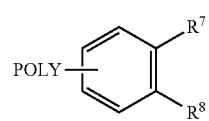

VI where (i) $R^7$ is C(=O)—CHR$^1$—NH—B, and $R^8$ is selected from —C(=O)OH, —CH$_2$OH, —C(=O)N(R$^1$)$_2$, —CH$_2$N(R$^1$)$_2$, —OH, and —N(R$^1$)$_2$, and is preferably selected from —C(=O)OH, —CH$_2$OH, —C(=O)N(R$^1$)$_2$, and —CH$_2$N(R$^1$)$_2$; or (ii) $R^7$ is —CHR$^1$—C(=O)—CHR$^1$—NH—B, and $R^8$ is —OH or —N(R$^1$)$_2$;

POLY is a water soluble polymer, such as a PEG, which may include a linker moiety, as described herein, linking it to the aromatic ring; and —NH—B represents the residue of an amine-containing biologically active compound; where each $R^1$ is independently selected from H, lower alkyl, and alkoxyalkyl, and preferably from H and methyl.

In general, preferred embodiments of the conjugates IV, V and VI are derived from preferred embodiments of the corresponding reagents I/Ia, II and III as described herein.

In particularly preferred embodiments, the conjugates are derived from self-catalyzing reagents. These include conjugates of structures IV and VI above, as well as conjugates of structure V above in which one group $R^2$ or $R^3$ is selected from hydroxy, alkoxy, amino, hydroxyalkyl, alkoxyalkyl, alkoxyalkylene, aminoalkyl, iminoalkyl, carboxylic acid, alkylcarboxylic acid, phosphate, and alkylphosphate; and this group $R^2$ or $R^3$ and the value of m are selected such that an oxygen or nitrogen atom on $R^2$ or $R^3$ is separated from Cα by a four-bond path. Preferably, $R^2$ or $R^3$ is selected from aminoalkyl, iminoalkyl, carboxylic acid, and alkylcarboxylic acid.

Certain conjugates derived from self-catalyzing reagents can also be represented by the structure VIII (derived from reagent structure VII above):

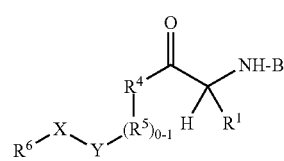

VIII where $R^1$ is selected from H, lower alkyl, and alkoxyalkyl;

$R^4$ and $R^5$ are carbon atoms, each of which is substituted with two groups selected from hydrogen, alkyl, alkenyl, alkoxy, a non-interfering substituent (e.g. halo, cyano, aryl or substituted aryl) and a water soluble polymer; Y is carbon, X is nitrogen or oxygen, and $R^6$ is selected from an electron pair, hydrogen, alkyl, alkenyl, alkoxy, and a water soluble polymer; such that (a) Y—X—$R^6$ represents a carboxyl, alkoxylalkyl, aminoalkyl, or iminoalkyl(ene) moiety, where Y—X may be part of a cyclic structure in the case of aminoalkyl or iminoalkyl(ene), or (b) X—$R^6$ taken alone represents amino or hydroxyl;

wherein $R^4$ and $R^5$ taken together, or $R^5$ and Y taken together, or $R^4$ and Y taken together when $R^5$ is absent, may form one side of a five- or six-membered ring which may be substituted with a water soluble polymer;

and wherein the reagent comprises at least one water soluble polymer;

and —NH—B represents the residue of an amine-containing biologically active compound.

Preferred embodiments of such conjugates include those corresponding to embodiments described for reagent structure VII, above.

V. The Conjugated Amine-Containing Agent

The biologically active agent conjugated to a polymeric reagent of the invention may fall into one of a number of structural classes, including but not limited to small molecules (including difficultly soluble small molecules), peptides, polypeptides, proteins, polysaccharides, steroids, nucleotides, oligonucleotides, polynucleotides, fats, electrolytes, and the like. The molecule either possesses a native amino group or is modified to contain at least one reactive amino group suitable for coupling to a polymeric reagent of the invention.

The agent may be a therapeutic substance selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

Specific examples of active agents suitable for covalent attachment to a polymer of the invention include aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase α, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, α-glucosidase, collagen, cyclosporin, alpha defensins, beta defensins, exedin-4, granulocyte colony stimulating factor (GCSF), thrombopoietin (TPO), α-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin).

Additional agents suitable for covalent attachment to a polymer of the invention include but are not limited to amifostine, amiodarone, aminocaproic acid, aminohippurate sodium, aminoglutethimide, aminolevulinic acid, aminosalicylic acid, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine, vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents such as penicillin G and penicillin V; penicllinase-resistant agents such as methicillin, oxacillin, cloxacillin, dicloxacillin, floxacillin, and nafcillin; gram negative microorganism active agents such as ampicillin, amoxicillin, and hetacillin, cillin, and galampicillin; antipseudomonal penicillins such as carbenicillin, ticarcillin, azlocillin, mezlocillin, and piperacillin; cephalosporins such as cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforamide, cefotaxime, cefatrizine, cephacetrile, cefepime, cefixime, cefonicid, cefoperazone, cefotetan, cefinetazole, ceftazidime, loracarbef, and moxalactam; monobactams such as aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

Preferred small molecules for coupling to a polymeric reagent of the invention are those having at least one amino group. Preferred molecules include aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine.

Preferred peptides or proteins for coupling to a polymeric reagent of the invention include EPO, IFN-alpha, IFN-beta, IFN-gamma, consensus IFN, Factor VII, Factor VIII, Factor IX, IL-2, remicade (infliximab), Rituxan (rituximab), Enbrel (etanercept), Synagis (palivizumab), Reopro (abciximab), Herceptin (trastuzimab), tPA, Cerizyme (imiglucerase), Hepatitus-B vaccine, rDNAse, alpha-1 proteinase inhibitor, GCSF, GMCSF, hGH, insulin, FSH, and PTH.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof. The above biologically active proteins are additionally meant to encompass variants having one or more amino acids substituted, deleted, or the like, as long as the resulting variant protein possesses at least a certain degree of activity of the parent (native) protein.

The reactive polymeric reagents of the invention may be attached, either covalently or non-covalently, to a number of solid entities including films, chemical separation and purification surfaces, solid supports, metal/metal oxide surfaces, such as gold, titanium, tantalum, niobium, aluminum, steel, and their oxides, and silicon oxide. Additionally, the polymers of the invention may also be used in biochemical sensors, bioelectronic switches, and gates. The polymeric reagents of the invention may also be employed as carriers for peptide synthesis, for the preparation of polymer-coated surfaces and polymer grafts, to prepare polymer-ligand conjugates for affinity partitioning, to prepare cross-linked or non-cross-linked hydrogels, and to prepare polymer-cofactor adducts for bioreactors.

VI. Pharmaceutical Compositions and Administration Methods

The invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form. The pharmaceutical preparations encompass all types of formulations and in particular those that are suited for injection, e.g., powders that can be reconstituted as well as suspensions and solutions.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000.

The pharmaceutical preparations of the present invention are typically, although not necessarily, administered via injection and are therefore generally liquid solutions or suspensions immediately prior to administration. The conjugates can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intraarterial, and so forth.

The invention also provides methods for administering a conjugate as provided herein to a patient suffering from a condition that is responsive to treatment with the conjugated agent. The method comprises administering, generally via injection, a therapeutically effective amount of the conjugate (preferably provided as part of a pharmaceutical preparation). The actual dose to be administered will vary depend upon the age, weight, and general condition of the subject, as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

Optimally, cleavage of the water-soluble polymer portion, which may be desirable to facilitate clearance from the body, can be facilitated through the incorporation of one or more physiologically cleavable and/or enzymatically degradable linkages such as urethane, amide, carbonate or ester-containing linkages, as described above, into the polymer component. In this way, clearance of the conjugate (via cleavage of individual water-soluble polymer portions) can be modulated by selecting the polymer molecular size and the type of linkage that would provide the desired clearance properties. One of ordinary skill in the art can determine the proper molecular size of the polymer as well as the cleavable functional group. Clearance properties can be evaluated by preparing a series of polymer derivatives with different polymer weights and cleavable functional groups, and then obtaining clearance profiles (e.g., through periodic blood or urine sampling) by administering the polymer derivatives to a patient and taking periodic blood and/or urine sampling.

EXPERIMENTAL

Example 1

Preparation of mPEG$_{5000}$-6-O-galactopyranose (1)

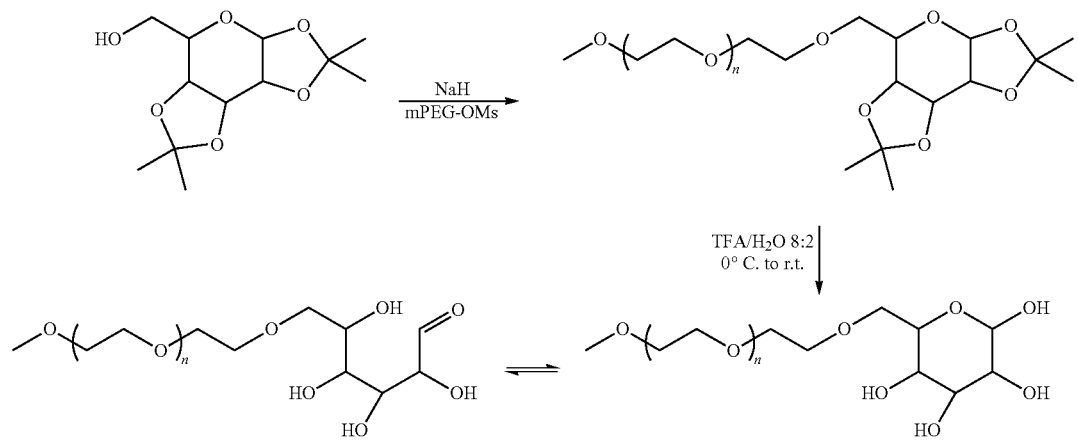

Hemiacetal form of an alpha-hydroxyaldehyde

Methoxy-polyethylene glycol (MW 5,000 Daltons) (M-PEG-OH, 5 kD, 8 g, 1.6 mmol) in 50 mL of anhydrous toluene was azeotropically distilled under reduced pressure at 60° C. on a rotary evaporator. The azeotropic distillation was repeated with 50 mL of anhydrous toluene and evaporated to approximately 25 mL. To the solution was added 10 mL of anhydrous methylene chloride and anhydrous triethylamine (0.39 mL, 2.8 mmol). The solution was stirred at room temperature under argon for 5 minutes and 0.179 mL of dry methanesulfonyl chloride (2.3 mmol) was added dropwise. The solution was stirred at room temperature under argon overnight. The mixture was evaporated under vacuum to remove methylene chloride and filtered over a bed of Celite to remove salts. The Celite was washed with additional toluene and the combined filtrate was evaporated under vacuum. The solids were dissolved in approximately 15 mL of methylene chloride and precipitated on ice by the addition of isopropanol. The precipitated product was filtered off, washed with diethylether and dried under reduced pressure. Yield 7.7 g $^1$H-NMR ($d_6$-DMSO, 400 MHz): δ (ppm) 3.18 (s, 3H, —SO$_2$—CH$_3$); 3.24 (s, 3H, —OCH$_3$); 3.51 (s, PEG backbone); 4.31 (—CH2-OMs).

Deprotection: The product above (2 g, 0.36 mmol) was dissolved at 0° C. in 10 mL of 8:2 trifluoroacetic acid/water and stirred 1 hour under an argon atmosphere. The reaction was stopped by the addition of 10 mL phosphate buffer (0.2 M, pH 9.1) and then neutralized to pH 6.8 with 3.0 M sodium hydroxide. The solution was diluted with an equal amount of half saturated sodium chloride and extracted 2 times with methylene chloride (200 mL). The combined organic layers were dried over anhydrous sodium sulfate/anhydrous magnesium sulfate, filtered and evaporated under reduced pressure. The solids were dissolved in 5 mL methylene chloride and precipitated with 65 mL isopropanol and 20 mL diethylether at 0° C. The precipitated product was filtered off, washed with diethylether containing 0.3% 2,6-di-tert-butyl-4-methyl-phenol and dried under vacuum. Yield 1.85 g.

$^1$H-NMR ($d_6$-DMSO+$D_2$O, 400 MHz): δ (ppm) 3.24 (s, 3H, —OCH$_3$); 3.51 (s, PEG backbone); 3.94 (t); 4.23 (d); 4.92 (d).

Example 2

Preparation mPEG$_{5000}$-3-O-D-glucose (2)

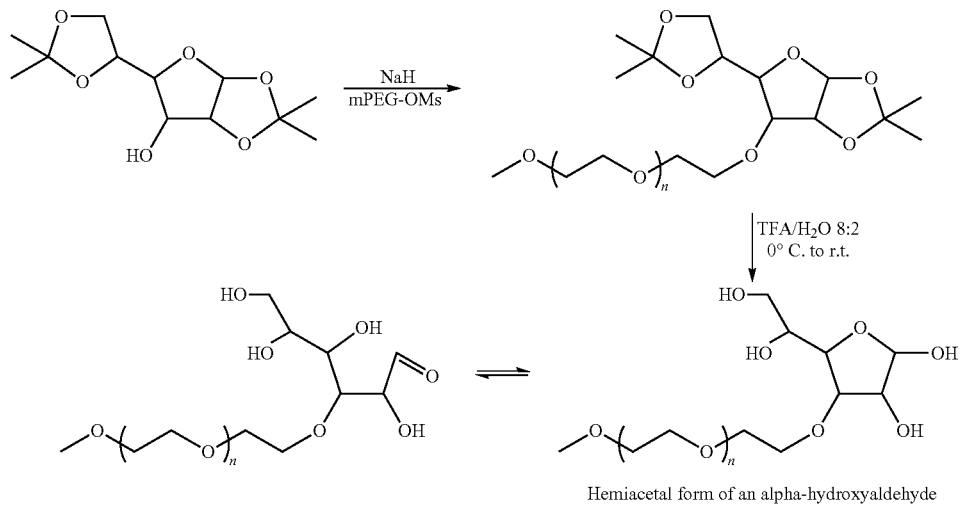

Hemiacetal form of an alpha-hydroxyaldehyde

M-PEG-OMs (5 kD, 3 g, 0.6 mmol), prepared as described above, in 20 mL of anhydrous toluene was azeotropically distilled under reduced pressure at 60° C. on a rotary evaporator. The azeotropic distillation was repeated with 30 mL of anhydrous toluene and evaporated to approximately 10 mL. To the solution was added 0.47 mL of 1,2:3,4-di-O-isopropylidene-D-galactopyranose (2.0 mmol) and 0.77 g of sodium hydride, 60% dispersion in mineral oil (19.3 mmol). The reaction was heated at 75° C. with stirring overnight under an argon atmosphere. The reaction mixture was cooled to room temperature, diluted with methylene chloride and filtered over a bed of Celite. The Celite was washed with additional methylene chloride and the combined filtrate was evaporated under vacuum. The solids were dissolved in 18 mL of 1:1 methylene chloride/toluene and precipitated by the addition of 100 mL isopropanol and 40 mL diethylether at 0° C. The precipitated product was filtered off, washed with diethylether and dried under reduced pressure. Yield 3.15 g $^1$H-NMR (CDCl$_3$, 400 MHz): δ (ppm) 1.21 (d, 6H, (O)$_2$C(CH$_3$)$_2$); 1.44 (s, 3H), 1.53 (s, 3H) ((O)$_2$C(CH$_3$)$_2$); 3.38 (s, 3H, —OCH$_3$); 3.64 (s, PEG backbone); 3.81 (t, 1H); 4.26 (m, 1H); 4.30 (m, 1H); 4.58 (m, 1H); 5.53 (d, 1H).

mPEG-OMs (5 kD, 7.7 g, 1.5 mmol), prepared as described in Example 1, in 50 mL of anhydrous toluene was azeotropically distilled under reduced pressure at 60° C. on a rotary evaporator. The azeotropic distillation was repeated with 60 mL of anhydrous toluene and evaporated to approximately 50 mL. To the solution was added 1.35 g of diacetone-D-glucose (5.2 mmol) and 0.2 g of sodium hydride 60% dispersion in mineral oil (5.0 mmol). The reaction was heated at 75° C. with stirring overnight under an argon atmosphere. The reaction mixture was cooled to room temperature, diluted with methylene chloride and filtered over a bed of Celite. The Celite was washed with additional methylene chloride and the combined filtrate was evaporated under vacuum. The solids were dissolved in 15 mL of methylene chloride and precipitated by the addition of 95 mL isopropanol and 95 mL diethylether at 0° C. The precipitated product was filtered off, washed with diethylether and dried under reduced pressure. Yield 7.3 g $^1$H-NMR (CDCl$_3$): δ (ppm) 1.31 (s, 3H), 1.35 (s, 3H), 1.42 (s, 3H) 1.49 (s, 3H) ((O)$_2$C(CH$_3$)$_2$); 3.38 (s, 3H, —OCH$_3$); 3.64 (s, PEG backbone); 3.92 (d, 1H); 3.98 (m, 1H); 4.07 (m, 1H); 4.11 (m, 1H); 4.30 (m, 1H); 4.57 (d, 1H); 5.87 (d, 1H).

Deprotection: The product above (2.5 g, 0.36 mmol) was dissolved at 0° C. in 10 mL of 8:2 trifluoroacetic acid/water and stirred 1 hour under an argon atmosphere. The reaction was stopped by the addition of 10 mL phosphate buffer (0.2 M, pH 9.1) and then neutralized to pH 6.8 with 3.0 M sodium hydroxide. The solution was diluted with an equal amount of half saturated sodium chloride and extracted 2 times with methylene chloride (200 mL). The combined organic layers were dried over anhydrous sodium sulfate/anhydrous magnesium sulfate, filtered and evaporated under reduced pressure. The solids were dissolved in 5 mL methylene chloride and precipitated with 65 mL isopropanol and 20 mL diethylether at 0° C. The precipitated product was filtered off, washed with diethylether containing 0.3% 2,6-di-tert-butyl-4-methyl-phenol and dried under vacuum. Yield 1.85 g $^1$H-NMR (d$_6$-DMSO+D$_2$O, 400 MHz): δ (ppm) 2.9 to 3.2 (m); 3.24 (s, 3H, —OCH$_3$); 3.51 (s, PEG backbone); 4.29 (d); 4.89 (d).

Example 3

Preparation and Conjugation of a "Self Catalyzing" Reagent (3)

A. Preparation of 2-hydroxy-3-amino-4-(2-imidazoyl)-butanal

The following synthetic scheme is employed to prepare the title compound (shown in protected form):

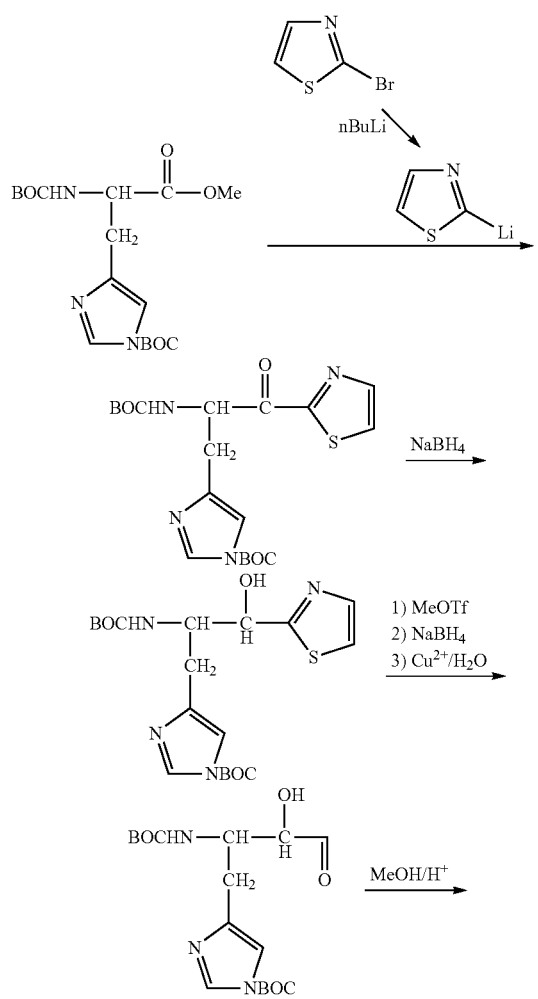

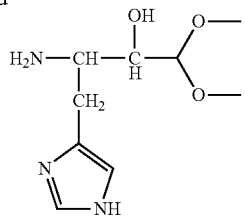

This compound is reacted with mPEG-SPA (the N-hydroxy succinimidyl ester of methoxypoly(ethylene glycol) propionic acid) to provide the amide-linked PEGylated reagent 3 (second compound in the scheme below).

This reagent can be reacted with a protein, according to procedures described above, to give the stable keto-amine conjugate shown.

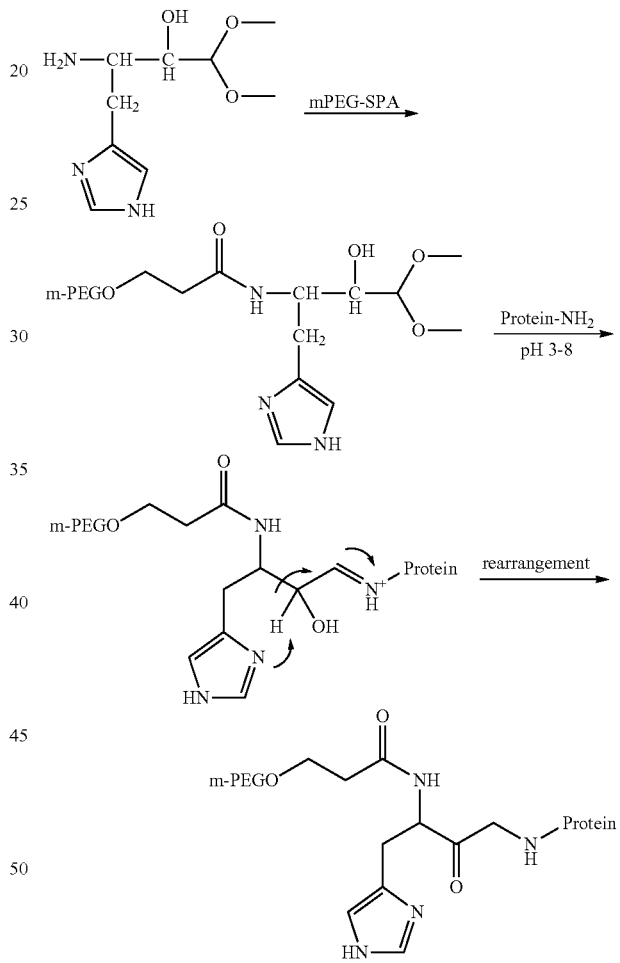

Example 4

Preparation of 5-mPEG$_{10000}$-2-hydroxypentanal (mPEG-HP-ALD 10 kD) (4)

This reagent was prepared according to the scheme below.

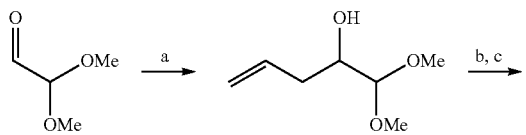

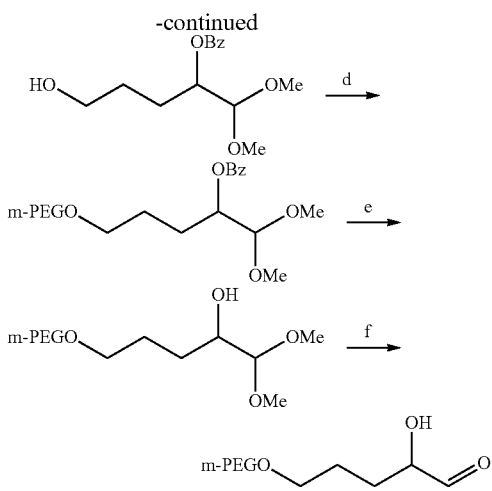

a) allyl bromide, In (powder), ethanol, 40° C.; b) benzyl bromide, NaH, DMF; c) 9-BBN, DCM, H$_2$O$_2$/NaOH; d) mPEG-OMs 10K, NaH, toluene, 50° C.; e) sodium phosphate, Pd/C, H$_2$; f) 10% phosphoric acid (a). Preparation of 2-hydroxy-1,1-dimethoxypent-4-ene (see D. Crestia et al., *Tetrahedron: Asymmetry* 12:869-876, 2001)

Indium powder (0.17 mol, 0.75 eq., 20 g, 100 mesh) was added to an ethanol (200 mL) solution containing 2,2-dimethoxyacetaldehyde (0.23 mol, 1.0 eq., 35 mL, 60 wt % solution in water) and allyl bromide (0.28 mol, 1.2 eq., 24 mL). The suspension was stirred at 40° C. for 3 h. The slurry was then centrifuged and the supernatant was decanted. The residual pellet was suspended in and washed 3 times with ethanol (3×150 mL). The combined supernatants were filtered and evaporated at reduced pressure to provide a thick oil (45° C., clear yellow oil, 56 g). The crude product resulting (25 g) was extracted with brine and ethyl acetate (2×). The combined organic layers were dried over sodium sulfate, filtered and evaporated at reduced pressure. Yield was 11 g (89%) of semi-purified oil. The product was purified by silica chromatography with a hexanes/ethyl acetate gradient on a Biotage SP-4 (FLASH 40+M) purification system. Purified yield 5.2 g (42%) clear colorless oil.

$^1$H-NMR (CDCl$_3$, 300 MHz): δ (ppm) 5.9 (m, 1 H, CH$_2$=CH—); 5.2 (m, 2 H, CH$_2$=CH—); 4.2 (d, 1 H, —CH(OCH$_3$)$_2$); 3.7 (m, 1 H, —CH(OH)—); 3.4 (ds, 6 H, —OCH$_3$); 2.3 (dm, 2 H, —CH$_2$—).

(b). Preparation of 2-hydroxybenzyl ester-1,1-dimethoxypentan-5-ol

In a dry flask 2-hydroxy-1,1-dimethoxypent-4-ene (2.92 g, 20 mmol) was dissolved in anhydrous DMF (40 mL). Sodium hydride (1.0 g, 25 mmol, 1.25 eq, 60 wt % dispersion in mineral oil) and benzyl bromide (2.73 mL, 23 mmol, 1.15 eq) were added with stirring under an inert nitrogen atmosphere. After 2.5 hours, the reaction was carefully quenched by slow addition of water. The product was extracted with brine and ethyl acetate (2×). The combined organic layers were washed with brine (3×), dried over sodium sulfate and evaporated at reduced pressure. Crude yield 4.8 g (100%) clear oil.

$^1$H-NMR (CD$_2$Cl$_2$, 300 MHz): δ (ppm) 7.3 (bm, 5 H, Ar); 5.9 (m, 1 H, CH$_2$=CH—); 5.1 (m, 2 H, CH$_2$=CH—); 4.6 (dd, 2 H, —CH$_2$—Ar); 4.2 (d, 1 H, —CH(OCH$_3$)$_2$); 3.5 (m, 1 H, —CH(OBz)-); 3.4 (ds, 6 H, —OCH$_3$); 2.3 (dm, 2 H, —CH$_2$—).

(c). The crude 2-hydroxybenzyl ester-1,1-dimethoxypent-4-ene (4.2 g, 17.8 mmol, 1.0 eq) was dissolved in dichloromethane (40 mL) containing 9-BBN (0.5M in THF, 82 mL, 41 mmol, 2.3 eq) under an inert nitrogen atmosphere. After 2 hours, a mixture of 30% hydrogen peroxide solution (25 mL) and 15% sodium hydroxide (25 mL) was added by slow dropwise addition. (Note: Caution gas and heat evolution; add reagent mixture slowly and carefully.) The reaction was stirred for an additional 3 hours and then extracted with brine and ethyl acetate (2×150 mL). The combined organic layers were washed with brine (3×), dried over sodium sulfate, filtered and evaporated at reduced pressure. Crude yield was 7.0 g (155%) of clear oil. The crude product was dissolved in methanol (70 mL)/water (3.5 mL) and washed with hexanes (3×70 mL). The combined hexane layers were back extracted with methanol (20 mL)/water (1 mL). The methanol layers were combined and extracted with brine and ethyl acetate (2×150 mL). The combined organic layers were washed with brine (2×) and dried over sodium sulfate, filtered and evaporated at reduced pressure. Yield 4.6 g (100%) of clear semi-purified oil. The semi-purified product was purified by silica chromatography with a hexanes/ethyl acetate gradient on a Biotage SP-4 (FLASH 40+M) purification system. Purified yield 2.5 g (55%) clear colorless oil.

$^1$H-NMR (CD$_2$Cl$_2$, 300 MHz): δ (ppm) 7.3 (bm, 5 H, Ar); 4.6 (dd, 2 H, —CH$_2$—Ar); 4.2 (d, 1 H, —CH(OCH$_3$)$_2$); 3.6 (t, 2 H, —CH$_2$—OH); 3.4 (ds, 6 H, —OCH$_3$; m, 1 H, —CH (OBz)-); 1.7 (m, 2 H, —CH$_2$—); 1.6 (m, 2 H, —CH$_2$—).

(d). A mixture of mPEG$_{10000}$-OMs (10 g, 1 mmol) and 2-hydroxybenzyl ester-1,1-dimethoxypentan-5-ol (0.51 g, 2 mmol, 2 eq) was prepared in 30 mL of anhydrous toluene and azeotropically distilled under reduced pressure at 50° C. on a rotary evaporator. The mixture was evaporated to dryness and then suspended in anhydrous toluene (30 mL) under an inert nitrogen atmosphere. Sodium hydride (0.11 g, 2.8 mmol, 2.8 eq, 60 wt % dispersion in mineral oil) was added and the reaction was heated to 75° C. The reaction was stirred at 75° C. for 24 hours then evaporated at reduced pressure. The thick oil was dissolved in dichloromethane (5 mL) and precipitated with the addition of isopropanol (300 mL). The precipitated product was filtered off, washed with isopropanol (75 mL), washed with diethylether (75 mL) and dried under reduced pressure. Yield was 9.8 g of an off-white powder.

$^1$H-NMR (CDCl$_3$, 300 MHz): δ (ppm) 7.3 (bm, 5 H, Ar); 4.6 (dd, 2 H, —CH$_2$—Ar); 4.2 (d, 1 H, —CH(OCH$_3$)$_2$); 3.6 (s, PEG backbone); 3.3 (s, 3 H, —OCH$_3$); 1.6 (bm, 4 H, —CH$_2$—CH$_2$—).

(e). In a Parr hydrogenation bottle 5-mPEG$_{10000}$-2-hydroxybenzyl ester-1,1-dimethoxypentane (2.5 g) was dissolved in sodium phosphate buffer (50 mM, pH 7.0, 50 mL). After sparging the solution with nitrogen, a 20% Pd/C paste (50.38% water, Pearlman's type, 0.5 g) was added to the bottle. The reaction mixture was hydrogenated (hydrogen gas at 20 psi) with stirring on a Parr apparatus. After 3 h hydrogen was removed from the reaction system by vacuum and the bottle was disconnected under a nitrogen flush. The suspension was filtered, rinsed with water and extracted with brine and dichloromethane (2×). The organic layers were combined, dried over anhydrous sodium sulfate, filtered and evaporated at reduced pressure to provide a viscous oil. The product was precipitated by the slow addition of diethyl ether. Yield 2.0 g off-white powder.

$^1$H-NMR (CDCl$_3$, 300 MHz): δ (ppm) 4.1 (d, 1 H, —CH(OCH$_3$)$_2$); 3.6 (s, PEG backbone); 3.3 (s, 3 H, —OCH$_3$); 1.7, 1.4, 1.2, 0.8 (m, 4 H, —CH$_2$—CH$_2$—).

(f). 5-mPEG$_{10,000}$-2-hydroxy-1,1-dimethoxypentane (1.6 g) was dissolved in 10% phosphoric acid (25 mL) and the solution was sparged with nitrogen. The hydrolysis reaction was stirred for 7 h and then adjusted to pH 6.9 with sodium hydroxide (1 M). The product was extracted with brine and dichloromethane (3×75 mL). The organic layers were combined, dried over anhydrous sodium sulfate, filtered and evaporated in vacuo to provide a viscous oil. The PEG material was dissolved in dichloromethane/isopropanol (1 mL:12 mL; containing butylated hydroxytoluene (BHT), 24 mg) and precipitated by addition of diethyl ether (70 mL). The filter cake was washed with diethyl ether (20 mL; containing BHT, 6 mg) and evaporated to dryness at reduced pressure. Yield 1.43 g off-white powder.

$^1$H-NMR (CDCl$_3$, 300 MHz): δ (ppm) 3.6 (s, PEG backbone); 3.3 (s, 3 H, —OCH$_3$); 1.7, 1.4, 1.2 (m, 4 H, —CH$_2$—CH$_2$—).

Example 5

Preparation of 5-mPEG$_{10K}$-methyl-amino)-2-hydroxypentanal (mPEG-MAHP-ALD 10 kD) (5)

This "self catalyzing" reagent was prepared according to the scheme below.

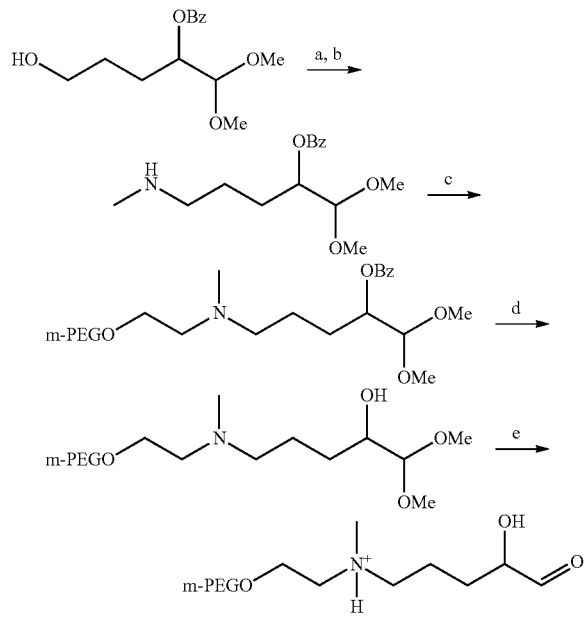

a) TEA, MsCl, toluene; b) ethanol, methyl amine 40% in water; c) mPEG-OMs 10K NaOH, water, THF, 50° C; d) sodium phosphate, Pd/C, H$_2$; e) 10% phosphoric acid (a). Preparation of 5-(methylamino)-2-hydroxybenzyl ester-1,1-dimethoxypentane In a dry flask 2-hydroxybenzyl ester-1,1-dimethoxypentan-5-ol (0.62 g, 2.4 mmol) was dissolved in anhydrous toluene (25 mL). Triethylamine (0.4 mL, 2.9 mmol) and methane sulfonyl chloride (0.2 mL, 2.55 mmol) were added to the reaction at room temperature. The reaction was stirred under inert atmosphere for 2.5 h. The slurry was filtered (0.45 micron syringe filter; rinsed with toluene) and the solvent was evaporated at reduced pressure. Yield 0.89 g crude oil.

$^1$H-NMR (CDCl$_3$, 300 MHz): δ (ppm) 7.3 (bm, 5 H, Ar); 4.6 (dd, 2 H, —CH$_2$—Ar); 4.3 (d, 1H, —CH(OCH$_3$)$_2$); 4.2 (t, 2 H, —CH$_2$—OMs); 3.4 (ds, 6 H, —OCH$_3$; m, 1 H, —CH(OBz)-); 3.0 (s, 3 H, —OMs); 1.9-1.6 (m, 4 H, —CH$_2$—CH$_2$—).

(b). The crude oil 5-[methanesulfonyl oxy-ester]-2-hydroxybenzyl ester-1,1-dimethoxypentane (0.89 g) was dissolved in anhydrous ethanol (4 mL). Methyl amine (40% solution in water, 25 mL) was added and the reaction mixture was stirred for 20 h. The reaction was extracted with brine and dichloromethane (2×). The combined organic layers were dried over anhydrous sodium sulfate, filtered and evaporated at reduced pressure. Yield 0.65 g oil.

$^1$H-NMR (CDCl$_3$, 300 MHz): δ (ppm) 7.3 (bm, 5 H, Ar); 4.6 (dd, 2 H, —CH$_2$—Ar); 4.2 (d, 1 H, —CH(OCH$_3$)$_2$); 3.4 (ds, 6 H, —OCH$_3$; m, 1 H, —CH(OBz)-); 2.6 (t, 2 H, —N(CH$_3$)—CH$_2$—); 2.4 (s, 3 H, —N(CH$_3$)—); 1.7-1.5 (m, 4 H, —CH$_2$—CH$_2$—).

(c). In a flask equipped with a reflux condenser, 5-[methylamino]-2-hydroxybenzyl ester-1,1-dimethoxypentane (0.65 g, 2.4 mmol) was dissolved in tetrahydrofuran (7 mL) and deionized water (5 mL). M-PEG-OMs (10 kD, 3.5 g, 0.35 mmol) and sodium hydroxide were added with stirring. The temperature was held at 50° C. for 16 h then additional tetrahydrofuran (7 mL) and deionized water (3.5 mL) were added. The reaction was continued at 50° C. for 24 h and then refluxed in an 85° C. bath for 4 h. The product was extracted with brine and dichloromethane (3×). The organic layers were combined, dried over anhydrous sodium sulfate, filtered and evaporated to a thick oil at reduced pressure. The product was precipitated by the slow addition of diethyl ether. Yield 2.94 g off-white powder.

$^1$H-NMR (D$_2$O, 300 MHz): δ (ppm) 7.3 (bm, 5 H, Ar); 4.6 (dd, 2 H, —CH$_2$—Ar); 4.3 (d, 1 H, —CH(OCH$_3$)$_2$); 3.6 (bs, PEG backbone); 3.3 (s, 3 H, —OCH$_3$); 2.6 (m, 2 H, —CH$_2$—N(CH$_3$)—); 2.3 (m, 2 H, —N(CH$_3$)—CH$_2$—); 2.1 (s, 3 H, —NH(CH$_3$)—); 1.5-1.3 (m, 4 H, —CH$_2$—CH$_2$—).

(d). In a Parr hydrogenation bottle 5-[mPEG$_{10000}$-methyl-amino]-2-hydroxybenzyl ester-1,1-dimethoxypentane (2.9 g) was dissolved in sodium phosphate buffer (50 mM, pH 7.0, 74 mL). The solution was sparged with nitrogen and 20% Pd/C paste (50.4% water, Pearlman's type, 0.59 g) was added to the bottle. The reaction mixture was hydrogenated (hydrogen gas at 20 psi) with stirring on a Parr apparatus. After 30 h hydrogen was removed from reaction system by vacuum and the bottle was disconnected under a nitrogen flush. The suspension was filtered, rinsed with water and extracted with brine and dichloromethane (3×). The organic layers were combined, dried over anhydrous sodium sulfate, filtered and evaporated to a thick oil at reduced pressure. The product was precipitated by the slow addition of diethyl ether. Yield 2.3 g off-white powder.

The crude PEG product (1.4 g) was purified by ion exchange chromatography on POROS media (0.2 L, Boehringer-Mannheim, BmbH, Mannheim Germany). The amine PEG product was bound to the column and then eluted with sodium chloride (5% solution). The desired product fractions were extracted with phosphoric acid, brine and dichloromethane (3×). The organic layers were combined, dried over anhydrous sodium sulfate, filtered and evaporated to a viscous oil at reduced pressure. The product was precipitated by the slow addition of diethyl ether. Yield 0.81 g of an off-white powder.

$^1$H-NMR (D$_2$O, 300 MHz): δ (ppm) 4.3 (d, 1 H, —CH(OCH$_3$)$_2$); 3.6 (bs, PEG backbone); 3.3 (s, 3 H, —OCH$_3$); 3.2 (m, 2 H, —N(CH$_3$)—CH$_2$—); 2.9 (s, 3 H, —NH(CH$_3$)—); 1.9-1.5 (m, 4 H, —CH$_2$—CH$_2$—).

(e). 5-[mPEG$_{10000}$-methyl-amino]-2-hydroxy-1,1-dimethoxypentane (0.7 g) was dissolved in 10% phosphoric acid (15 mL) and the solution was sparged with nitrogen. The hydrolysis reaction was stirred for 28 h and then adjusted to pH 4.5 with sodium hydroxide (1 M). The product was extracted with brine and dichloromethane (3×75 mL). The organic layers were combined, dried over anhydrous sodium sulfate, filtered and evaporated to a viscous oil at reduced pressure. The oil yielded an amorphous solid after slow addition with stirring of diethyl ether (50 mL). This suspension was evaporated to dryness at reduced pressure. Yield 0.54 g of an off-white powder.

$^1$H-NMR (D$_2$O, 300 MHz): δ (ppm) 3.6 (bs, PEG backbone); 3.3 (s, 3 H, —OCH$_3$); 3.2 (bm, 2 H, —N(CH$_3$)—CH$_2$—); 2.9 (s, 3 H, —NH(CH$_3$)—); (m, 4 H, —CH$_2$—CH$_2$—).

Example 6

Conjugation of Lysozyme with mPEG Reagents (a). Conjugation using mPEG Reagents with Aliphatic Aldehyde (Butyraldehyde) and α-hydroxy Aldehyde (HP-ALD Reagent 4)

Sodium phosphate buffers (0.2 M) were prepared at pH 6.5, ph 7.5 and pH 9.0. A lysozyme (Sigma Aldrich L-6876, EC 3.2.1.17) stock solution (10 mg/mL lysozyme) was also prepared in sodium phosphate buffer (20 mM, pH 7.5). The reactions in FIG. 1 were run by dissolution of the indicated PEG product (36 mg) in a mixture of lysozyme stock solution (0.1 mL) at the indicated pH by use of sodium phosphate buffer (0.2 M, 0.9 mL). Reactions labeled as including NaCNBH$_3$ additionally contained freshly prepared sodium cyanoborohydride stock solution (25 μL; 9 mg NaCNBH$_3$ in 1 mL sodium phosphate 0.2 M, pH 7.5). The reactions were mixed and incubated at r.t. for 18 h. Aliquots (3 μL) were taken and diluted with water and sample buffer (NuPAGE® LDS 4× buffer, Invitrogen, 6 μL).

The samples were loaded on a SDS-PAGE gel (Invitrogen NuPAGE® 4-12% Bis-Tris, running buffer MES 1×) and run at 200 V for 45 min. The gels were removed, rinsed, stained with SimplylBlue™ SafeStain (Invitrogen) for 1 h and then destained for more than 2 h. Results are shown in FIG. 1, with lanes as indicated below:
1) Benchmark ladder,
2) lysozyme (Lyz),
3) Lyz+mPEG$_{10000}$-HP-ALD (4), pH 6.5,
4) Lyz+mPEG$_{10000}$-HP-ALD (4), pH 7.5,
5) Lyz+mPEG$_{10000}$-HP-ALD (4), pH 9.0,
6) Lyz+mPEG$_{10000}$-HP-ALD (4), pH 7.5+NaCNBH$_3$,
7) Lyz+mPEG$_{20000}$-butyrALD (20 kD), pH 7.5,
8) Lyz+mPEG$_{20000}$-butyrALD (20 kD), pH 7.5+NaCNBH$_3$.

As can be seen from the gel (FIG. 1), conversion of the protein (low migration band) to the conjugate (band around the midpoint of the gel) increased as the pH of the reaction was increased (lanes 3-5), in the reaction with the α-hydroxy aldehyde (HP-ALD) reagent.

No conjugation product was detectable in the reaction of protein and PEG-butyraldehyde alone (lane 7), since the expected imine product is very sensitive to hydrolysis. A detectable product, the reduced amine, did form in the presence of a reducing agent (NaCNBH$_3$) (lane 8).

(b). Conjugation Using mPEG Reagents with α-hydroxy Acetal (HP-ALD 4 Acetal) and "Self-Catalyzing" (MAHP) Reagent (5)

Figure 2:
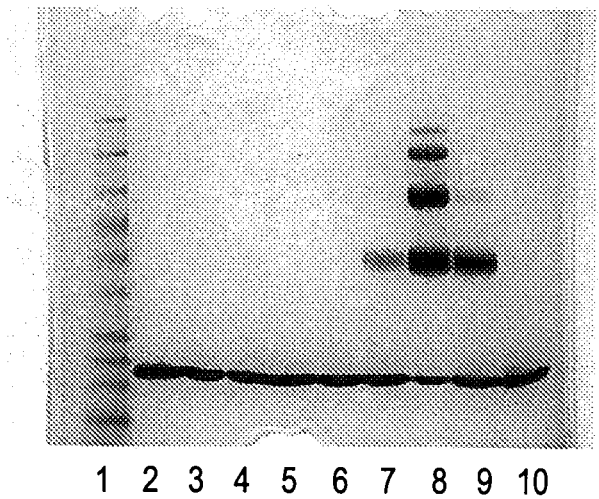
FIG. 2 shows an SDS-PAGE gel obtained from electrophoresis of reaction mixtures of conjugation reactions of Lysozyme (1 mg/mL) and the polymeric reagents mPEG$_{10K}$-HP-acetal (acetal of invention compound 4), mPEG$_{10K}$-MAHP-ALD (invention compound 5, "self-catalyzing") and its acetal, run under different reaction conditions, as described in Example 6b.
Lane:
1) Benchmark ladder,
2) lysozyme (Lyz),
3) Lyz+mPEG$_{10K}$-HP (4) acetal, pH 6.5,
4) Lyz+mPEG$_{10K}$-HP (4) acetal, pH 9.0,
5) Lyz+mPEG$_{10K}$-MAHP (5) acetal, pH 6.5,
6) Lyz+mPEG$_{10K}$-MAHP (5) acetal, pH 9.0,
7) Lyz+mPEG$_{10K}$-MAHP-ALD (5), pH 6.5,
8) Lyz+mPEG$_{10K}$-MAHP-ALD (5), pH 9.0,
9) Lyz+mPEG$_{10K}$-MAHP (5) acetal (purified, 95% sub), pH 6.5,
10) Lyz+mPEG$_{10K}$-MAHP (5) acetal (purified, 95% sub), pH 9.0.

The reactions in FIG. 2 were conducted in a similar manner with the indicated mPEG reagent (10 mg) in a mixture of lysozyme stock solution (0.03 mL) and sodium phosphate buffer (0.2 M, 0.27 mL). The reactions were mixed and incubated at r.t. for 24 h. Aliquots (3.5 μL) were taken, and diluted with water and sample buffer (NuPAGE® LDS 4× buffer, Invitrogen, 6 μL).

The samples were loaded on a SDS-PAGE gel (Invitrogen NuPAGE® 4-12% Bis-Tris, running buffer MES 1×) and run at 200 V for 42 min. The gels were removed, rinsed, stained with SimplyBlue™ SafeStain (Invitrogen) for 1 h and then destained for more than 2 h. Results are shown in FIG. 2, with lanes as indicated below:
1) Benchmark ladder,
2) lysozyme (Lyz),
3) Lyz+mPEG$_{10000}$-HP (4) acetal, pH 6.5,
4) Lyz+mPEG$_{10000}$-HP (4) acetal, pH 9.0,
5) Lyz+mPEG$_{10000}$-MAHP (5) acetal, pH 6.5,
6) Lyz+mPEG$_{10000}$-MAHP (5) acetal, pH 9.0,
7) Lyz+mPEG$_{10000}$-MAHP-ALD (5), pH 6.5,
8) Lyz+mPEG$_{10000}$-MAHP-ALD (5), pH 9.0,
9) Lyz+mPEG$_{10000}$-MAHP (5) acetal (purified, 95% sub), pH 6.5,
10) Lyz+mPEG$_{10000}$-MAHP (5) acetal (purified, 95% sub), pH 9.0.

As can be seen, the mPEG$_{10000}$-MAHP-ALD reagent (5) (lanes 7-8) showed the greatest amount of conjugation of all reagents tested thus far, with increased reaction at higher pH. (The acetal is expected to be unreactive at higher pH, but could undergo deprotection to the reactive aldehyde at the lower pH. The purification procedure noted for lane 9 could have also caused some deprotection to the aldehyde.)

(c). Further Conjugation Reactions Using Mpeg Reagents with Aliphatic Aldehyde (Butyraldehyde), α-hydroxy Aldehyde (HP-ALD, 4) and "Self-Catalyzing" (MAHP) Reagent (5)

Figure 3:
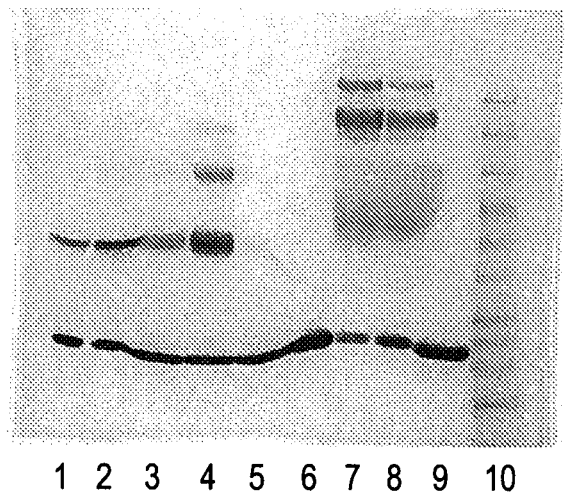
FIG. 3 shows an SDS-PAGE gel obtained from electrophoresis of reaction mixtures of conjugation reactions of a protein, lysozyme (1 mg/mL), with the polymeric reagents mPEG$_{10K}$-HP-ALD (invention compound 4), mPEG$_{10K}$-MAHP-ALD (invention compound 5, "self-catalyzing") and its acetal, and mPEG$_{10K}$-butyrALD (prior art compound), run under different reaction conditions, as described in Example 6c.
Lane:
1) Lyz+mPEG$_{10K}$-HP-ALD (4), pH 6.5,
2) Lyz+mPEG$_{10K}$-HP-ALD (4), pH 7.5,
3) Lyz+mPEG$_{10K}$-MAHP-ALD (5) (purified, 95% sub), pH 6.5,
4) Lyz+mPEG$_{10K}$-MAHP-ALD (5) (purified, 95% sub), pH 7.5,
5) Lyz+mPEG$_{10K}$-MAHP (5) acetal (purified, 95% sub), pH 7.5,
6) Lyz+mPEG$_{20K}$-butyrALD, pH 7.5,
7) Lyz+mPEG$_{20K}$-butyrALD, pH 6.5+NaCNBH$_3$,
8) Lyz+mPEG$_{20K}$-butyrALD, pH 7.5+NaCNBH$_3$
9) lysozyme,
10) Benchmark ladder.

The reactions in FIG. 3 were run by dissolution of the indicated PEG product (10-20 mg) in a mixture of lysozyme stock solution (0.03 mL) and the indicated pH of sodium phosphate buffer (0.2 M, 0.27 mL). Reactions labeled as including NaCNBH$_3$ additionally contained freshly prepared sodium cyanoborohydride stock solution (7.5 μL; 9 mg NaCNBH$_3$ in 1 mL sodium phosphate 0.2 M, pH 6.5 or pH 7.5 as needed). The reactions were mixed and incubated at r.t. for 18 h. Aliquots (3.5 μL) were taken, and diluted with water and sample buffer (NuPAGE® LDS 4× buffer, Invitrogen, 6 μL). The samples were loaded on a SDS-PAGE gel (Invitrogen NuPAGE® 4-12% Bis-Tris, running buffer MES 1×) and run at 200 V for 45 min. The gels were removed rinsed, stained with SimplyBlue™ SafeStain (Invitrogen) for 1 h and then destained for more than 2 h. Results are shown in FIG. 3, with lanes as indicated below:
1) Lyz+mPEG$_{10K}$-HP-ALD (4) (10 kD), pH 6.5,
2) Lyz+mPEG$_{10K}$-HP-ALD (4) (10 kD), pH 7.5,
3) Lyz+mPEG$_{10K}$-MAHP-ALD (5) (purified, 95% sub), pH 6.5,
4) Lyz+mPEG$_{10K}$-MAHP-ALD (5) (purified, 95% sub), pH 7.5,
5) Lyz+mPEG$_{10K}$-MAHP (5) acetal (purified, 95% sub), pH 7.5,
6) Lyz+mPEG$_{20K}$-butyrALD (20 kD), pH 7.5,
7) Lyz+mPEG$_{20K}$-butyrALD (20 kD), pH 6.5+NaCNBH$_3$,
8) Lyz+mPEG$_{20K}$-butyrALD (20 kD), pH 7.5+NaCNBH$_3$,
9) lysozyme,
10) Benchmark ladder.

Again, reaction with the "self-catalyzing" reagent, mPEG-MAHP-ALD (5), at higher pH (lane 4) gave the greatest amount of conjugation. No reaction was seen with the butyraldehyde reagent in the absence of NaCNBH$_3$ (lanes 6-8). The simple α-hydroxy aldehyde reagent, mPEG-HP-ALD (4), gave a moderate amount of conjugation (lanes 1-2).

Example 7

Preparation of 5-mPEG$_{20K}$-2-hydroxy-pentanal or PEG-m HP-ALD (9)

This reagent (a higher molecular weight version of reagent 4) was prepared according to the scheme below.

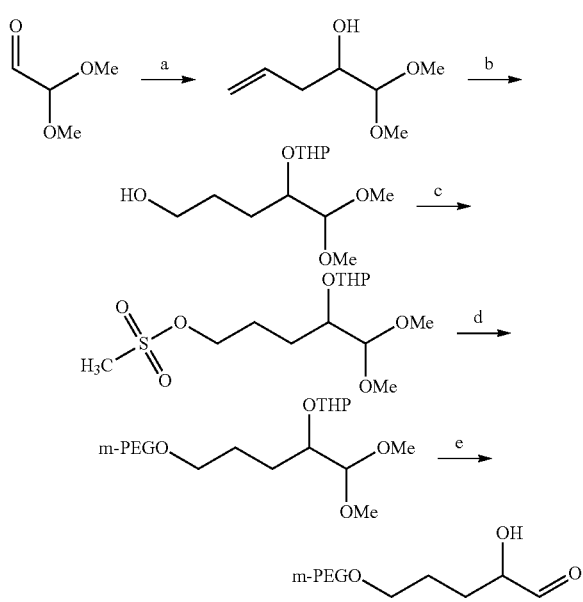

a) allyl bromide, In (powder), ethanol, 40° C.; b) 3,4-dihydro-2h-pyran, pyridinium p-toluenesulfonate, DCM; 9-BBN, DCM, H₂O₂/NaOH; c) methanesulfonyl chloride, TEA, toluene; d) mPEG—OH 20K, NaH, toluene, 45° C.; e) 20% phosphoric acid (a) Preparation of 2-hydroxy-1,1-dimethoxy-pent-4-ene (Crestia et al., 2001)

Indium powder (0.52 mol, 1 eq., 60 g, 100 mesh) was added to an ethanol (250 mL) solution containing 2,2-dimethoxyacetaldehyde (0.52 mol, 1.0 eq., 90.62 g, 60 wt % solution in water) and allyl bromide (0.79 mol, 1.5 eq., 66.5 mL). The suspension was stirred at 40° C. for 3 h. The slurry was then centrifuged and the supernatant was decanted. The pellet was suspended and washed 3 times with ethanol (350, 350, and 450 mL). The combined supernatants were mixed with 1500 mL deionized water and 1500 mL saturated sodium chloride. The crude product was extracted with chloroform (1500, 300 mL). The combined organic layers were washed with 1500 mL saturated sodium chloride. The chloroform extract was dried over sodium sulfate, filtered and evaporated at reduced pressure. Yield 40.4 g (53% yield) product.

$^1$H-NMR (CDCl$_3$, 500 MHz): δ (ppm) 5.9 (m, 1 H, CH$_2$=CH—); 5.2 (m, 2 H, CH$_2$=CH—); 4.2 (d, 1 H, —CH (OCH$_3$)$_2$); 3.7 (m, 1 H, —CH(OH)—); 3.4 (d, 6 H, —OCH$_3$); 2.3 (dm, 2 H, —CH$_2$—). (b)

(c) Preparation of 2-hydroxytetrahydropyranyl-1,1-dimethoxy-pentan-5-ol

In a dry flask 2-hydroxy-1,1-dimethoxy-pent-4-ene (38.84 g, 0.266 mol) was dissolved in toluene and azeotropically dried by distilling solvent (at 40° C.) until oil remained. The material was dissolved in anhydrous dichloromethane (780 mL). 3,4-dihydro-2h-pyran (48.2 mL, 0.532 mol) and pyridinium p-toluenesulfonate (3.34 g, 0.013 mol) were added. The reaction was monitored with thin layer chromatography (Mobile phase: 60/40 ethyl acetate-hexanes, Vanillin stain). After 20 hrs, 3,4-dihydro-2h-pyran (5.0 mL, 0.06 mol) was added. The reaction was complete 3 hours after last addition of 3,4-dihydro-2h-pyran. The reaction solution was washed with saturated sodium bicarbonate solution (2×200 mL). The dichloromethane extract was dried with sodium sulfate, filtered, and evaporated at reduced pressure Crude yield: 61.67 g (100%), clear oil.

$^1$H-NMR (CDCl3, 500 MHz): δ (ppm) 5.9 (m, 1 H, CH$_2$=CH—); 5.1 (m, 2 H, CH$_2$=CH—); 4.7, 4.9 (t, 1 H, —CH); 4.2, 4.4 (dd, 1 H, —CH); 4.0 (m, 1 H, —CH); 3.8, 3.5 (m, 2H, —CH$_2$ from THP); 3.4 (d, 6H, (OCH$_3$)$_2$); 2.4 (m, 2 H, —CH$_2$—); 1.5-1.8 (m, 6 H, THP moiety).

The crude 2-hydroxytetrahydropyranyl-1,1-dimethoxy-pentan-5-ol (58.76 g, 0.255 mol) was dissolved in toluene (600 mL) and distilled until oil remained. The oil was dissolved in dichloromethane (500 mL). 9-BBN (0.5M in THF, 816 mL, 0.408 mol) was added under an inert nitrogen atmosphere. After 2 hours, a mixture of 30% hydrogen peroxide solution (500 mL) and 15% sodium hydroxide (500 mL) was added by slow dropwise addition. (Note: Caution gas and heat evolution; add reagent mixture slowly and carefully.) The reaction was stirred for an additional 4 hours and washed reaction mixture with saturated sodium chloride (1000 mL, 400 mL). The organic layer was dried over sodium sulfate, filtered and evaporated at reduced pressure. The crude product was dissolved in methanol (1700 mL) with water (83 mL) and washed with hexanes (3×750 mL). The methanol/water layer (bottom layer) was mixed with saturated sodium chloride/deionized water/1M sodium hydroxide (1800 mL) and the product extracted with dichloromethane (1700 mL, 1000 mL). The organic extract was dried with sodium sulfate, filtered and evaporated at reduced pressure. Yield 80.14 g (100%) of clear semi-purified oil. A sample of the semi-purified product (5 g) was purified by silica chromatography with a methanol/dichloromethane gradient on a Biotage SP-4 (FLASH 40+M) purification system. Purified yield 3.4 g (70%) clear colorless oil.

$^1$H-NMR (DMSO, 500 MHz): δ (ppm) 4.6-4.7 (t, 1 H, —CH); 4.3, 3.3, (m, 2 H, —CH$_2$); 4.2, 4.3 (d, 1 H, —CH); 3.8 (m, 1 H, —CH); 3.5, 3.4 (m, 2 H, —CH$_2$); 3.3 (ss, 6H, —O(CH$_3$)$_2$); 1.8-1.3 (m, 10H, —CH$_2$CH$_2$ and THP moiety).

(d) Preparation of 2-hydroxytetrahydropyranyl-1,1-dimethoxy-pentan-5-methanesulfonate In a dry flask 2-hydroxytetrahydropyranyl-1,1-dimethoxy-pentan-5-ol (4 g, 0.016 mol) was dissolved in toluene and azeotropically dried by distilling solvent (at 40° C.) until oil remained. The material was dissolved in anhydrous toluene (152 mL). Triethylamine (2.65 mL, 0.019 mol) and methanesulfonyl chloride (1.33 mL, 0.017 mol) were added. After 20 hours, the solution was filtered and washed with 1:1 deionized water/saturated sodium bicarbonate (2×400 mL). The toluene extract was dried with sodium sulfate, filtered, and evaporated at reduced pressure Crude yield: 5.21 g (96%), clear oil.

$^1$H-NMR (DMSO, 500 MHz): δ (ppm) 4.6-4.7 (t, 1 H, —CH); 4.2, (m, 2 H, —CH$_2$; 4.2, 4.3 (d, 1 H, —CH); 3.8 (m, 1 H, —CH); 3.6, 3.5 (m, 2 H, —CH$_2$); 3.3 (s, 6H, —(OCH$_3$)$_2$); 3.1 (s, 3H, —CH$_3$); 1.8-1.3 (m, 10H, —CH$_2$CH$_2$ and THP moiety)

(e) Preparation of 5-mPEG(20,000)-2-hydroxytetrahydropyranyl-1,1-dimethoxypentane A mixture of mPEG-OH 20K (36.15 g, 1.8 mmol) and 2-hydroxytetrahydropyranyl-1,1-dimethoxy-pentan-5-methanesulfonate (3.0 g, 9.1 mmol) were dissolved in 360 mL of anhydrous toluene and azeotropically distilled under reduced pressure at 45° C. on a rotary evaporator. The mixture was evaporated to dryness and then suspended in anhydrous toluene (100 mL with 100 mg BHT) under an inert nitrogen atmosphere. Sodium hydride (0.360 g, 9 mmol, 60 wt % dispersion in mineral oil) was added and the reaction was heated to 45° C. The reaction was stirred at 45° C. for 67 hours. Additional sodium hydride (0.2 g, 8.3 mmol) was added, and the reaction was stirred at 45° C. for an additional 48 hours, then evaporated at reduced pressure. The thick oil was precipitated with the addition of isopropanol (2000 mL). The precipitated product was filtered, washed with isopropanol (750 mL), washed with diethyl ether (1000 mL), and dried under reduced pressure. Yield 23.1 g off-white powder (64% recovery).

$^1$H-NMR (CDCl$_3$, 500 MHz): δ (ppm) 4.8, 4.7 (t, 1, —CH); 4.4, 4.2 (d, 1 H, —CH); 4.0 (m, 1 H, —CH); 3.6 (s, PEG backbone); 3.3 (s, 3 H, —OCH$_3$); 1.8-1.4 (m, 8 H, —CH$_2$THP moeity).

(f) Preparation of 5-mPEG(20,000)-2-hydroxy-pentanal 5-mPEG(20,000)-2-hydroxytetrahydropyranyl-1,1-dimethoxypentane (23.1 g, 1.2 mmol) was dissolved in 500 mL of 20% phosphoric acid solution in water. After 20 hours, the pH of the mixture was adjusted to 6.80 with 50% sodium hydroxide/water. Salts were filtered (due to saturated phosphate salts) and the product was extracted with dichloromethane. The dichloromethane extract was dried with sodium sulfate, filtered, and evaporated to a thick oil. Isopropanol/BHT solution was added to the oil. The precipitated material was filtered and washed with isopropanol/BHT solution. The product was washed with diethyl ether/BHT and dried under reduced pressure. Yield 18.0 g off-white powder.

$^1$H-NMR (CDCl$_3$, 500 MHz): δ (ppm) 9.7 (s, 1H, H—C═O); 4.2 (t, 1H, —CH); 3.6 (s, PEG backbone); 3.3 (s, 3 H, —OCH$_3$); 1.7-1.8 (m, 4 H, —CH$_2$—CH$_2$—).

Example 8

Preparation of 5-mPEG$_{20,000}$-methylamino-2-hydroxy-pentanal (or mPEG-MAHP-ALD 20K) (10)

This reagent (a higher molecular weight version of reagent 5) was prepared according to the scheme below.

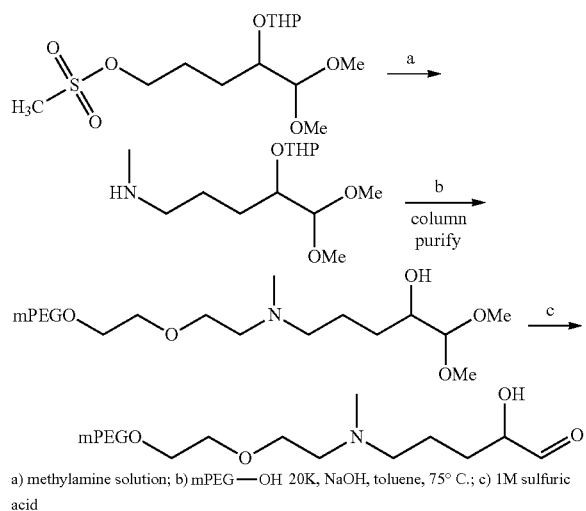

a) methylamine solution; b) mPEG—OH 20K, NaOH, toluene, 75° C.; c) 1M sulfuric acid (a) Preparation of 2-hydroxytetrahydropyranyl-1,1-dimethoxy-pentan-5-methylamine In a dry flask 2-hydroxytetrahydropyranyl-1,1-dimethoxy-pentan-5-methanesulfonate (8.5 g, 0.016 mol) was dissolved in ethanol (40 mL). Methylamine (40% in water, 255 mL) was added. After 17 hours at room temperature, saturated sodium chloride solution (300 mL) was added. The product was extracted with dichloromethane (300 mL). The dichloromethane extract was dried with sodium sulfate, filtered, and evaporated under reduced pressure. Yield: 7.03 g (100%), clear oil.

$^1$H-NMR (DMSO, 500 MHz): δ (ppm) 4.6,4.7 (t,1H,—CH); 4.3,4.2 (d,1H,—CH); 3.8 (m,1H, —CH); 3.5,3.4 (m,2H, —CH$_2$); 3.4 (d, 6H, (OCH$_3$)$_2$), 2.4 (m, 2H, —CH$_2$); 1.8-1.3 (m,10H, THP moiety and CH$_2$CH$_2$).

(b) Preparation of 5-mPEG(20,000)-2-hydroxy-1,1-dimethoxy-pentan-5-methylamine

In a dry flask mPEG-mesylate 20K (25.0 g, 1.25 mmol) was dissolved in toluene (100 mL). Sodium hydroxide (0.5 g, 12.5 mmol) and 2-hydroxytetrahydropyranyl-1,1-dimethoxy-pentan-5-methylamine (3.3 g, 12.63 mmole) were added. The temperature of the reaction was 75° C. After 49 hours, diethyl ether (1000 mL) was added. The product was filtered and washed with diethyl ether (200 mL). The extract was dried with sodium sulfate. The product was filtered and dried under reduced pressure. Yield: 23 g (92%), clear oil.

$^1$H-NMR (DMSO, 500 MHz): δ (ppm) 4.6,4.7 (t,1H,—CH); 4.3,4.2 (d,1H,—CH); 3.8 (m,1H, —CH); 3.6 (s, PEG-backbone); 3.2 (s, 3H, OCH$_3$), 2.2 (s, 3H, —CH$_3$), 1.8-1.3 (m, 10H, THP moiety and CH$_2$CH$_2$).

Crude 5-mPEG(20,000)-2-hydroxytetrahydropyranyl-1,1-dimethoxy-pentan-5-methylamine (22.5 g, 1.13 mmol) was dissolved in deionized water (1500 mL). The solution was passed through desalting media (Purolite®). Conductivity was 8.71 μS/cm and pH: 8.09. The solution was loaded onto POROS HS 50 (cation exchange resin, 1300 mL). The column was washed with deionized water (approximately 1 column volume). Sodium chloride solution (5%) was used to elute product from POROS HS 50 media. The solution pH was adjusted to 2.70 with dilute sodium hydroxide solution. The product was extracted with dichloromethane, and the dichloromethane extract was dried with sodium sulfate, filtered and concentrated under reduced pressure overnight. Yield: 14 g (62% recovery).

$^1$H-NMR (D$_2$O, 300 MHz): δ (ppm) 4.3 (d, 1 H, —CH (OCH$_3$)$_2$), 3.6 (bs, PEG backbone); 3.3 (s, 3 H, —OCH$_3$); 3.2 (m, 2 H, —N(CH$_3$)—CH$_2$—); 2.9 (s, 3 H, —NH(CH$_3$)—); 1.9-1.5 (m, 4 H, —CH$_2$—CH$_2$—).

(c) Preparation of 5-mPEG(20,000)-methylamino-2-hydroxy-pentanal

In a dry flask 5-mPEG(20,000)-2-hydroxy-1,1-dimethoxy-pentan-5-methylamine (12.63 g, 0.63 mmol) was dissolved in 1M sulfuric acid (51 mL). After 20 hours, deionized water (440 mL) and 10% phosphoric acid (126 mL) were added. Sodium chloride (61 g) was added and the pH of the solution was adjusted to 2.8 with 1M sodium hydroxide. The product was extracted with dichloromethane (300, 100 mL). The organic extracts were dried with sodium sulfate and filtered. The filtrate was distilled to a thick oil and product was then precipitated with isopropanol/BHT solution. The wet cake was washed with isopropanol/BHT solution. The cake was washed with diethyl ether/BHT solution, filtered, and dried under reduced pressure. Yield: 11.7 g (93%), clear oil.

$^1$H-NMR (D$_2$O (with trifluoroacetic acid spike), 300 MHz): δ (ppm) 3.6 (bs, PEG backbone); 3.3 (s, 3 H, —OCH$_3$); 3.2 (bm, 2 H, —N(CH$_3$)—CH$_2$—); 2.9 (s, 3 H, —NH(CH$_3$)—); 1.9-1.5 (m, 4 H, —CH$_2$—CH$_2$—).

Example 9

Preparation of 5-mPEG$_{10,000}$-piperazine-2-hydroxy-pentanal or mPEG-Pip-HP-ALD 10K) (11)

This reagent was prepared according to the scheme below.

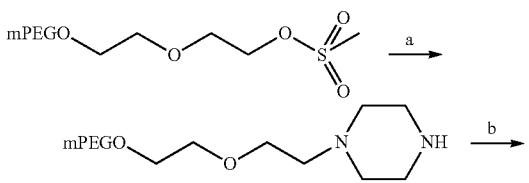

-continued mPEGO~O~N(piperazine)N~~~CH(OTHP)-CH(OMe)2 c → mPEGO~O~N(piperazine)N~~~CH(OH)-CHO a) piperazine, water; b) 2-hydroxytetrahydropyranyl-1,1-dimethoxy-pentan-5-methanesulfonate, dioxane, 1M sodium hydroxide; c) 1M sulfuric acid (a) Preparation of mPEG-piperazine 10K In a round bottom flask, mPEG-mesylate 10K (31.0 g, 3.1 mmol) was dissolved in a solution of piperazine (18.65 g, 216.5 mmol) in 95 mL deionized water. After 48 hours, saturated sodium chloride (100 mL) and deionized water (100 mL) were added. The product was extracted with dichloromethane (60, 60, 30 mL). The organic extracts were combined and dried with sodium sulfate, and the solution was filtered and distilled to a thick oil. The product was precipitated with 1:1 isopropanol/diethyl ether containing BHT, washed with isopropanol/diethyl ether/BHT solution, and dried under vacuum. Yield: 29.6 g (95% recovery).

$^1$H-NMR (DMSO, 500 MHz): δ (ppm) 3.6 (s, PEG backbone); 3.3 (s, 3H, —OCH$_3$); 2.6 (t,4H, CH$_2$—CH$_2$); 2.4 (t, 2H, —CH$_2$); 2.3 (t, 4H, CH$_2$—CH$_2$).

(b) Preparation of 5-mPEG(10,000)-piperazine-2-hydroxytetrahydropyranyl-1,1-dimethoxypentane In a round bottom flask, mPEG-piperazine 10K (1.09 g, 0.11 mmol) and 2-hydroxytetrahydropyranyl-1,1-dimethoxy-pentan-5-methanesulfonate (0.192 g, 0.59 mmol) were dissolved in 1,4-dioxane (1.3 mL) 1M sodium hydroxide solution (1.3 mL). After 22 hours at 50° C., deionized water (10 mL) and saturated sodium chloride solution (25 mL) were added. The product was extracted with dichloromethane (2×20 mL). The dichloromethane extract was dried with sodium sulfate and filtered. The filtrate was distilled to a thick oil and precipitated with isopropanol. Diethyl ether and methyl-tert butyl ether were added to help with filtration. The product was placed under vacuum to dry. Yield: 0.6 g (61% recovery).

$^1$H-NMR (DMSO, 500 MHz): δ (ppm) 4.6,4.7 (t, 1H, —CH); 4.2, 4.3 (d, 1H, —CH); 3.8 (m, 1H, —CH); 3.6 (s, PEG backbone), 3.2 (s, 3H, —OCH$_3$); 2.42 (t, 2H, —CH$_2$); 1.8-1.3 (m, 10H, THP moiety and —CH$_2$—CH$_2$).

(c) Preparation of 5-mPEG(10,000)-piperazine-2-hydroxypentanal (or mPEG-Pip-HP-ALD 10K)

In a round bottom flask, 5-mPEG(10,000)-piperazine-2-hydroxytetrahydropyranyl-1,1-dimethoxypentane (0.528 g, 0.053 mmol) was dissolved in 1M sulfuric acid (2.1 mL). After 19 hours at room temperature (approximately 21° C.), deionized water (20 mL) and 10% phosphoric acid (5 mL) were added. Sodium chloride (2.5 g) was added and the pH was adjusted to 2.5 with 1M sodium hydroxide. The product was extracted with dichloromethane. The dichloromethane extract was dried with sodium sulfate and filtered. The filtrate was distilled to a thick oil and precipitated with a 1:1 mixture of isopropanol and diethyl ether. The cake was washed with a 1:1 mixture of isopropanol and diethyl ether and placed under vacuum to dry.

Yield: 0.35 g (66% recovery). $^1$H-NMR (CDCl$_3$, 500 MHz): δ (ppm) 9.8 (s, 1 H, H—C=O); 3.6 (s, PEG backbone); 3.3 (s, 3H, OCH$_3$)

Example 10

Preparation of 5-mPEG$_{20,000}$-piperazine-2-hydroxypentanal (or mPEG-Pip-HP-ALD 20K) (12)

This reagent (a higher molecular weight version of reagent 11) was prepared according to the scheme below.

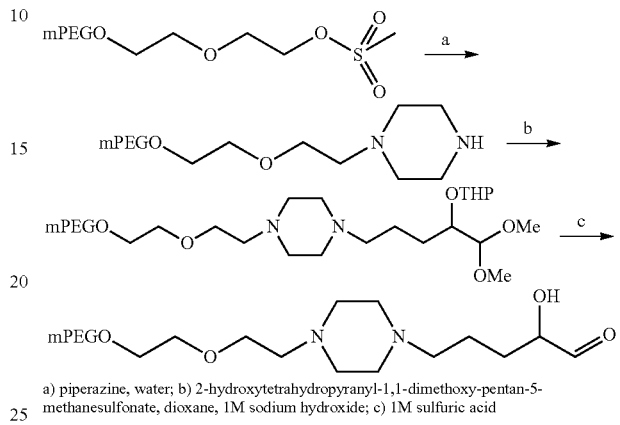

a) piperazine, water; b) 2-hydroxytetrahydropyranyl-1,1-dimethoxy-pentan-5-methanesulfonate, dioxane, 1M sodium hydroxide; c) 1M sulfuric acid (a) Preparation of mPEG-piperazine 20K In a round bottom flask, mPEG-mesylate 20K (40.5 g, 2.0 mmol) was dissolved in a solution of piperazine (25.2 g, 293 mmol) in 150 mL deionized water. After 19 hours, saturated sodium chloride (125 mL) and deionized water (125 mL) were added. The product was extracted with dichloromethane (60, 60, 30 mL), and the organic extracts were combined, washed with dilute sodium hydroxide and saturated sodium chloride (1:1, 400 mL), and dried with sodium sulfate. The solution was filtered and distilled to dryness. The product was dissolved in dichloromethane (80 mL) and precipitated with isopropanol containing BHT (1400 mL, 400 mg BHT). Methyl tert butyl ether (400 mL) was added to help with filtration. The product was washed with isopropanol/BHT solution and placed under vacuum to dry.

Yield: 37.3 g (95% recovery).

$^1$H-NMR (DMSO, 500 MHz): δ (ppm) 3.6 (s, PEG backbone); 3.3 (s, 3H, —OCH$_3$); 2.6 (t,4H, CH$_2$—CH$_2$); 2.4 (t, 2H, —CH$_2$); 2.3 (t, 4H, CH$_2$—CH$_2$).

(b) Preparation of 5-mPEG(20,000)-piperazine-2-hydroxytetrahydropyranyl-1,1-dimethoxypentane In a round bottom flask, mPEG-piperazine 20K (12.0 g, 0.6 mmol) and 2-hydroxytetrahydropyranyl-1,1-dimethoxy-pentan-5-methanesulfonate (1.06 g, 3.2 mmol) were dissolved in 1,4-dioxane (14.3 mL) and 1M sodium hydroxide (14.3 mL). After 24 hours at 50° C., 2-hydroxytetrahydropyranyl-1,1-dimethoxy-pentan-5-methanesulfonate (0.521 g, 1.6 mmol) were added, and reaction was continued for an additional 23 hours at 50° C. Deionized water (100 mL) and saturated sodium chloride solution (100 mL) were added. The product was extracted with dichloromethane (200, 100 mL). The dichloromethane extract was dried with sodium sulfate and filtered. The filtrate was distilled to a thick oil and precipitated with methyl-tert-butyl ether/BHT. The product was washed with methyl-tert-butyl-ether/BHT and placed under vacuum to dry. Yield: 11 g (92% recovery).

$^1$H-NMR (DMSO, 500 MHz): δ (ppm) 4.6,4.7 (t, 1H, —CH); 4.2, 4.3 (d, 1H, —CH); 3.8 (m, 1H, —CH); 3.6 (s, PEG backbone), 3.2 (s, 3H, —OCH$_3$); 2.42 (t, 2H, —CH$_2$); 1.8-1.3 (m, 10H, THP moiety and —CH$_2$—CH$_2$).

(c) Preparation of 5-mPEG$_{20K}$-piperazine-2-hydroxy-pentanal or mPEG$_{20K}$-Pip-HP-ALD)

In a round bottom flask, 5-mPEG(10,000)-piperazine-2-hydroxytetrahydropyranyl-1,1-dimethoxypentane (8.0 g, 0.4 mmol) was dissolved in 1M sulfuric acid (35 mL). After 18 hours at room temperature (approximately 21° C.), deionized water (250 mL) and 10% phosphoric acid (50 mL) were added. Sodium chloride (40 g) was added and the pH was adjusted to 2.5 with 1M sodium hydroxide. The product was extracted with dichloromethane (200, 100, 100 mL). The dichloromethane extract was dried with sodium sulfate and filtered. The filtrate was distilled to a thick oil and precipitated with a 1:1 mixture of isopropanol and methyl tert-butyl ether with BHT. The cake was washed with a 1:1 mixture of isopropanol and methyl tert-butyl ether with BHT and placed under vacuum to dry.

Yield: 7.4 g (93% recovery).

$^1$H-NMR (CD2Cl2, 500 MHz): δ (ppm) 9.7 (s, 1 H, H—C=O); 3.6 (s, PEG backbone); 3.3 (s, 3H, OCH$_3$)

Example 11

Conjugation of Lysozyme with mPEG$_{20K}$-MAHP-ALD (10) and mPEG$_{10K}$-Pip-HP-ALD (11)

Sodium phosphate buffer (100 mM) was prepared at pH: 6.0, 6.5, and 9.1. A separate Lysozyme (Aldrich, L-6786, EC 3.2.1.17) solution was prepared using 10 mM phosphate buffer pH: 7.0 (10 mg/mL buffer). The lysozyme solution was spiked into the 100 mM phosphate buffers (pH: 6.0, 6.5, and 9.1) to obtain a specific concentrations to react with the PEG.

The conjugation reactions were run by dissolution of the indicated PEG product (10 mg, 15 mg) in the 2 mg/mL and 1 mg/mL Lysozyme solutions. The reactions were incubated at room temperature for 24 hours. Aliquots were taken and diluted with 4×LDS buffer and deionized water to obtain solutions that were 0.75 mg Lysozyme/mL solution. The samples were loaded on a SDS-PAGE gel (Invitrogen NuPAGE® 4-12% BIS-TRIS, running buffer: MES SDS 1×). The samples were run at 200 V for 45 minutes. The gels were removed, rinsed and stained with SimplyBlue™ SafeStain (Invitrogen) for 1 hour and destained for more than 2 hours. Results are shown in FIG. 4, with lanes as indicated below:
1) Benchmark ladder,
2) Lysozyme (Lyz),
3) Lyz+mPEG-Pip-HP-ALD 10K (11), 25×, pH: 6.5,
4) Lyz+mPEG-Pip-HP-ALD 10K (11), 50×, pH: 6.5,
5) Lyz+mPEG-Pip-HP-ALD 10K (11), 50×, pH: 9.1,
6) Lyz+mPEG-Pip-HP-ALD 10K (11), 25×, pH: 6.0,
7) Lyz+mPEG-Pip-HP-ALD 10K (11), 50×, pH: 6.0,
8) Lyz+mPEG-MAHP-ALD 20K (10), 25×, pH: 6.5,
9) Lyz+mPEG-MAHP-ALD 20K (10), 50×, pH: 6.5,
10) Lyz+mPEG-MAHP-ALD 20K (10), 50×, pH: 9.1

Figure 4:
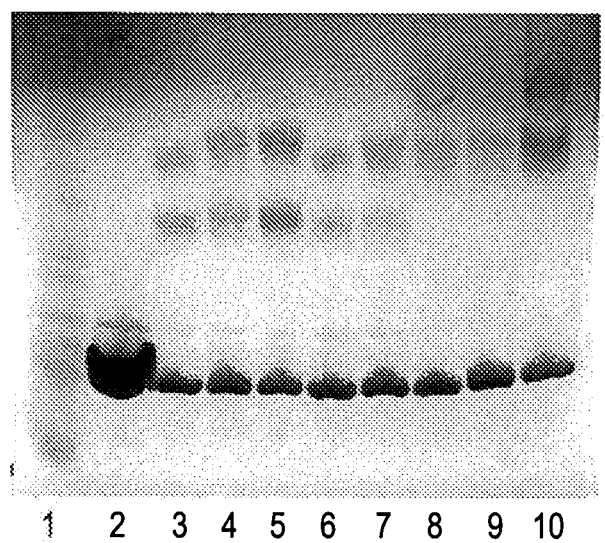
FIG. 4 shows an SDS-PAGE gel obtained from electrophoresis of reaction mixtures of conjugation reactions of a protein, lysozyme (1 mg/mL), with the polymeric reagents mPEG$_{20K}$-MAHP-ALD (invention compound 10, "self-catalyzing") and mPEG$_{10K}$-Pip-HP-ALD (invention compound II, "self-catalyzing"), run under different reaction conditions, as described in Example 11.
Lane:
1) Benchmark ladder,
2) Lysozyme (Lyz),
3) Lyz+mPEG$_{10K}$-Pip-HP-ALD (11), 25×, pH 6.5,
4) Lyz+mPEG$_{10K}$-Pip-HP-ALD (11), 50×, pH 6.5,
5) Lyz+mPEG$_{10K}$-Pip-HP-ALD (11), 50×, pH 9.1,
6) Lyz+mPEG$_{10K}$-Pip-HP-ALD (11), 25×, pH 6.0,
7) Lyz+mPEG$_{10K}$-Pip-HP-ALD (11), 50×, pH 6.0,
8) Lyz+mPEG$_{20K}$-MAHP-ALD (10), 25×, pH 6.5,
9) Lyz+mPEG$_{20K}$-MAHP-ALD (10), 50×, pH 6.5,
10) Lyz+mPEG$_{20K}$-MAHP-ALD (10), 50×, pH 9.1.

The results in FIG. 4 show evidence of monoPEGylated and diPEGylated conjugates of the protein were obtained using both reagents (with reagent 10 providing higher molecular weight conjugates, as expected). Greater amounts of conjugate were obtained at higher pH, which is consistent with the base-promoted self catalyzing feature of these reagents.

Example 12

Conjugation of Protein (55 kDa) with mPEG-HP-ALD 20K (9) and mPEG-MAHP-ALD 20K (10)

Conjugation to 5-mPEG(20,000)-2-hydroxy-pentanal (mPEG-HP-ALD 20K, 9) and "self catalyzing" reagent 5-mPEG(20,000)-methylamino-2-hydroxy-pentanal (mPEG-HP-MALD 20K, 10) was investigated further using a protein having a molecular weight of 55 kDa. Conjugation reactions were set up by mixing a known amount of protein, typically around 1 mg/mL, to each PEG reagent at a molar excess of approx. 20. The conjugation reactions were carried out at pH ranges of 6.5-9.0 using a 0.2M phosphate buffer containing sucrose and allowed to proceed for up to 16 hrs at 25° C.

The resulting conjugates were analyzed by SDS-PAGE. Briefly, 45 μL of each sample conjugate was mixed with 15 μL of 4×LDS NuPAGE® sample buffer and separated on a 4-12% BisTris NuPAGE® gel using the MES buffer system, with lanes as indicated below:
1) MW markers,
2) 1 μg mPEG-HP-ALD 20K (9),
3) 3 μg unmodified 55 kDa protein,
4) mPEG-HP-ALD 20K (9)/55 kDa protein; pH 6.5,
5) mPEG-HP-ALD 20K (9)/55 kDa protein; pH 7.5,
6) mPEG-HP-ALD 20K (9)/55 kDa protein; pH 9.0,
7) 1 μg mPEG-HP-MALD 20K (10),
8) 3 μg unmodified 55 kDa protein,
9) mPEG-HP-MALD 20K (10)/55 kDa protein; pH 6.5,
10) mPEG-HP-MALD 20K (10)/55 kDa protein; pH 7.5,
11) mPEG-HP-MALD 20K (10)/55 kDa protein; pH 9.0,
12) Blank.

Figure 5A:
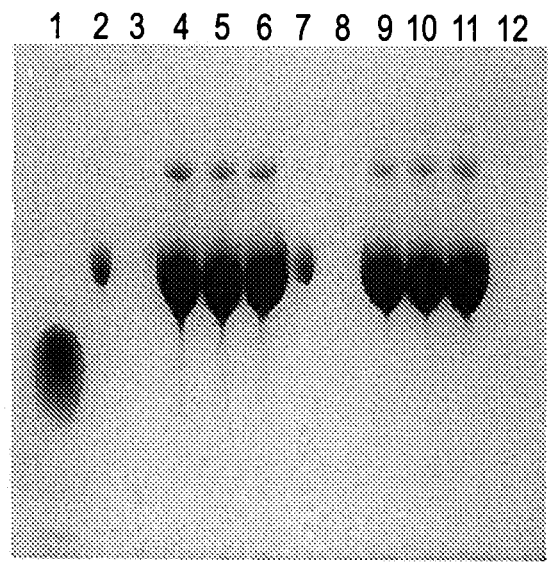
FIGS. 5A-B show SDS-PAGE gels obtained from electrophoresis of reaction mixtures of conjugation reactions of a 55 kDa protein (1 mg/mL) with the polymeric reagents mPEG$_{20K}$-HP-ALD (invention compound 9) and mPEG$_{20K}$-MAHP-ALD (invention compound 10, "self-catalyzing"), run under different reaction conditions, as described in Example 12.
Figure 5B:
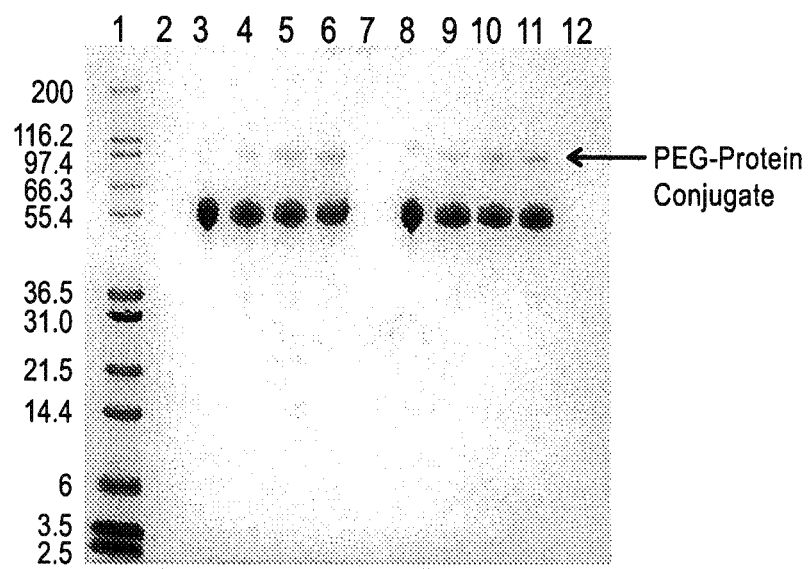

The data is shown in FIGS. 5A-B (5A: Barium/Iodine stain; 5B: Coomassie stain). The protein conjugate (for both panels) is indicated by the arrow to the right of the figure.

Example 13

Conjugation of Insulin with mPEG-MAHP-ALD 20K (10)

Conjugation of 5-mPEG$_{20,000}$-methylamino-2-hydroxy-pentanal (mPEG-HP-MALD 20K) was investigated using insulin. The conjugation reaction was performed with mPEG-MAHP-ALD 20K (25 mg) added into 0.5 mL, 3 mg/ml insulin solution (50% ethanol/water, pH 9.7). The reaction mixture was incubated at room temperature with stirring at 600 rpm. After 18 hours, aliquots were taken and analyzed by reverse phase HPLC (0.1% TFA water/acetonitrile gradient, Agilent Zorbax C18, UV 276 nm). HPLC results demonstrated 20% and 27% of mono and di-PEGylated insulin conjugate formed, respectively.

Example 14

Conjugation of Lysozyme with mPEG-HP-ALD 20K (9), mPEG-MAHP-ALD 20K (10), mPEG-Pip-HP-ALD 10K (11) and mPEG-butyraldehyde 20K (Varied pH and Temperature)

The conjugation reactions were conducted with the indicated mPEG reagents (21 mg, 50 eq.) dissolved in sodium phosphate buffer (0.2 M, 0.27 mL) followed by addition of lysozyme stock solution (0.03 mL, 10 mg/mL in 0.2M phosphate buffer). The reactions were mixed, split into 2 portions and incubated at either room temperature (approximately 21° C.) or 5° C. for 24 h or 48 h. Samples were frozen (−20° C.) until analyzed. Aliquots (4 μL) were taken and diluted with water and sample buffer (NuPAGE® LDS 4× buffer, Invitrogen, 6 μL). The samples were loaded on a SDS-PAGE gel (Invitrogen NuPAGE® 4-12% Bis-Tris, running buffer MES 1×) and run at 200 V for 42 min. The gels were removed, rinsed, stained with SimplyBlue™ SafeStain (Invitrogen) for at least 1 h and then destained for more than 2 h.

Figure 6A:
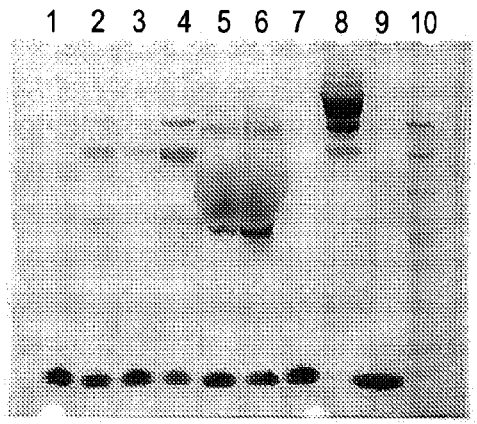
FIGS. 6A-B show SDS-PAGE gels obtained from electrophoresis of reaction mixtures of conjugation reactions of lysozyme (1 mg/mL) with the indicated polymeric reagents (50×) at pH 6.5 and 9.0 in 0.2 M phosphate buffer, as described in Example 14.
Figure 6B:
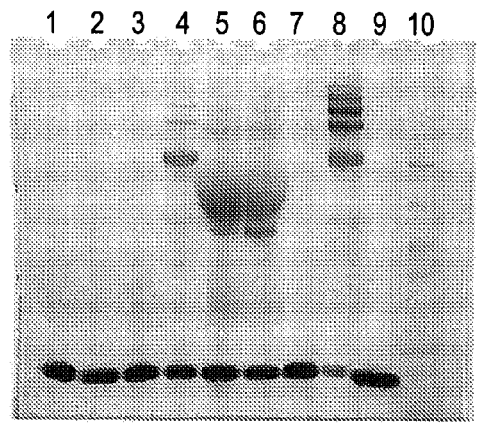

Results are shown in FIGS. 6A-B (6A: reaction at r.t. for 1 day; 6B; reaction at 5° C. for 1 day), with lanes as indicated below:
1) Lyz+mPEG-HP-ALD 20K (9), pH 6.5,
2) Lyz+mPEG-HP-ALD 20K (9), pH 9.0,
3 Lyz+mPEG-MAHP 20K (10), pH 6.5,
4) Lyz+mPEG-MAHP 20K (10), pH 9.0,
5) Lyz+mPEG-Pip-HP-ALD 20K (12), pH 6.5,
6) Lyz+mPEG-Pip-HP-ALD 20K (12), pH 9.0,
7) Lyz+mPEG-butryALD 20K, pH 6.5,
8) Lyz+mPEG-ButryALD 20K+ NaCNBH$_3$, pH 6.5.
9) lysozyme (Lyz),
10) Invitrogen Benchmark™ ladder, The reactions were repeated at pH 7.5 (0.2M sodium phosphate buffer or 0.2M HEPES buffer) at r.t. for one day. The samples were analyzed by on a SDS-PAGE as described above. Results are shown in FIG. 6C, with lanes as indicated below:
1) Lyz+mPEG-HP-ALD 20K (9), 0.2 M phosphate buffer, pH 7.5,
2) Lyz+mPEG-HP-ALD 20K (9), 0.2 M HEPES buffer, pH 7.5,
3 Lyz+mPEG-MAHP 20K (10), 0.2 M phosphate buffer, pH 7.5,
4) Lyz+mPEG-MAHP 20K (10), 0.2 M HEPES buffer, pH 7.5,
5) Lyz+mPEG-Pip-HP-ALD 20K (12), 0.2 M phosphate buffer, pH 7.5,
6) Lyz+mPEG-Pip-HP-ALD 20K (12), 0.2 M HEPES buffer, pH 7.5,
7) Lyz+mPEG-butryALD 20K, 0.2 M phosphate buffer, pH 7.5,
8) Lyz+mPEG-butryALD 20K, +NaCNBH$_3$, 0.2 M phosphate buffer, pH 7.5,
9) lysozyme,
10) Invitrogen Benchmark™ ladder.

Figure 6C:
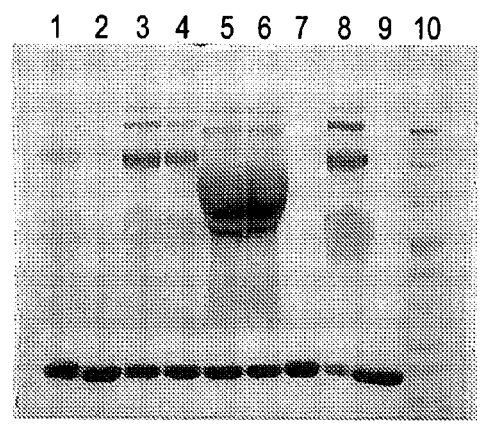
FIG. 6C shows SDS-PAGE gels obtained from electrophoresis of reaction mixtures of conjugation reactions of lysozyme (1 mg/mL) with the indicated polymeric reagents (50×) at pH 7.5, as also described in Example 14.
Lane:
1) Lyz+mPEG$_{NK}$-HP-ALD (9), 0.2 M phosphate buffer, pH 7.5,
2) Lyz+mPEG$_{20K}$-HP-ALD (9), 0.2 M HEPES buffer, pH 7.5,
3 Lyz+mPEG$_{20K}$-MAHP (10), 0.2 M phosphate buffer, pH 7.5,
4) Lyz+mPEG$_{20K}$-MAHP (10), 0.2 M HEPES buffer, pH 7.5,
5) Lyz+mPEG$_{20K}$-Pip-HP-ALD (12), 0.2 M phosphate buffer, pH 7.5,
6) Lyz+mPEG$_{20K}$-Pip-HP-ALD (12), 0.2 M HEPES buffer, pH 7.5, 7) Lyz+mPEG$_{20K}$-butryALD, 0.2 M phosphate buffer, pH 7.5,
8) Lyz+mPEG$_{20K}$-butryALD, +NaCNBH$_3$, 0.2 M phosphate buffer, pH 7.5,
9) lysozyme,
10) Benchmark ladder.

As can be seen from FIGS. 6A-C, the mPEG-MAHP-ALD 20K (10) and mPEG-Pip-HP-ALD 20K (12) reagents (self-catalyzing) showed the greatest amount of conjugation for the α-hydroxy aldehyde reagents tested thus far, with increased reaction at higher pH. The gels appear to show a coelution of the excess mPEG-Pip-HP-ALD 20K reagent (12) with the mono-PEG-lysozyme conjugate (lanes 5-6) which disturbed the expected migration for the mono-PEG product. (Compare gel of purified reaction mixture in FIG. 7; Example 17 below.) The di-PEG and tri-PEG lysozyme conjugates with mPEG-Pip-HP-ALD 20K (12) (higher migrating bands in lanes 5-6) demonstrated migration more similar to that observed for the other conjugates.

The reactions incubated at 5° C. (FIG. 6B) demonstrated qualitatively less conjugation product compared to incubations at room temperature (FIG. 6A), although lysozyme conjugate was observed for mPEG$_{20K}$-MAHP-ALD (10) at pH 9.0 (lane 4) and mPEG$_{20K}$-Pip-ALD (12) at pH 6.5 and pH 9.0 (lanes 5 and 6). As observed in previous experiments, the butyraldehyde reagent showed little or no conjugation in the absence of reducing agent (lane 7).

Example 16

Conjugation of Lysozyme at pH 6.5, 7.5 or 9.0 ALD 9, mPEG$_{20K}$mPEG$_{10K}$-Pip-HP-ALD (11) and mPEG$_{20K}$-Butryaldehyde The reactions summarized in Table 1 were conducted with the indicated mPEG 20K reagent (42 mg, 20 eq.) dissolved, as indicated, in sodium phosphate buffer (0.2 M, 1.35 mL, pH as indicated) followed by addition of lysozyme stock solution (0.15 mL, 10 mg/mL in the indicated buffer). The reactions were mixed and incubated at 25° C. for 20-24 h. Aliquots were taken and analyzed by reverse phase HPLC (0.1% TFA water/acetonitrile gradient, Agilent Zorbax 300SB C3, UV 280 nm). HPLC results demonstrated the following results for conjugate yields (relative area percent based on UV 280).

As observed previously, conjugation yields with the α-hydroxy reagents disclosed herein increased with pH, particularly for the "self-catalyzing" reagents. No conjugation was observed for the butyraldehyde reagent in the absence of reducing agent.

TABLE 1

HPLC analysis of Lysozyme Conjugation Reactions with PEG Aldehyde Reagents

| Reaction | mPEG reagent | pH | % Lysozyme | % Mono Conjugate | % Di Conjugate | % Tri Conjugate |
|---|---|---|---|---|---|---|
| 1 | HP-ALD | 6.5 | 90.2 | 7.1 | 1.1 | — |
| 2 | HP-ALD | 7.5 | 85.6 | 10.5 | 2.4 | — |
| 3 | HP-ALD | 9.0 | 78.0 | 16.4 | 3.8 | 0.6 |
| 4 | MAHP-ALD | 6.5 | 88.3 | 9.2 | 1.8 | — |
| 5 | MAHP-ALD | 7.5 | 77.0 | 15.3 | 5.3 | 0.9 |
| 6 | MAHP-ALD | 9.0 | 67.2 | 24.5 | 5.8 | 1.1 |
| 7 | Pip-HP-ALD | 6.5 | 88.1 | 6.2 | — | — |
| 8 | Pip-HP-ALD | 7.5 | 80.5 | 12.4 | ~2.4 | ~1.8 |
| 9 | Pip-HP-ALD | 9.0 | 70.4 | 20.6 | ~4.3 | ~1.8 |
| 10 | ButyrALD | 6.5 | 98.7 | — | — | — |
| 11 | ButyrALD + NaCNBH$_3$ | 6.5 | 35.3 | 45.6 | 14.4 | 2.4 |

Example 17

Conjugation of Lysozyme at pH 6.5, 7.5 or 9.0 with mPEG$_{20K}$-Pip-HP-ALD (12), with Removal of Excess PEG Reagent The reactions summarized in Table 2 were conducted with the indicated mPEG 20K reagent (104 mg, 50 eq.) dissolved, as indicated, in sodium phosphate buffer (0.2 M, 1.35 mL, pH as indicated) followed by addition of lysozyme stock solution (0.15 mL, 10 mg/mL in the indicated buffer). These reactions were similar to those summarized in lines 7-9 of Table 1, but with a higher excess of PEG reagent (50× vs. 20×). The reaction components were mixed and incubated at 25° C. for 20-24 h.

The reaction mixture was purified to remove excess PEG reagent, and the conjugates, including unreacted protein, were analyzed by reverse phase HPLC (0.1% TFA water/acetonitrile gradient, Agilent Zorbax 300SB C3, UV 280 nm). HPLC results demonstrated the following results for conjugate yields (relative area percent based on UV 280).

TABLE 2

HPLC Analysis of Purified mPEG$_{20K}$-Pip-HP-ALD (50x) Conjugation with Lysozyme at pH 6.5, 7.5 and 9.0

| mPEG-20K Reagent | pH | % Lysozyme | % Mono Conjugate | % Di Conjugate | % Tri Conjugate |
|---|---|---|---|---|---|
| Pip-HP-ALD | 6.5 | 83.1 | 15.4 | 1.5 | — |
| Pip-HP-ALD | 7.5 | 74.3 | 23.7 | 2 | — |
| Pip-HP-ALD | 9.0 | 64.0 | 32.6 | 3.4 | — |

Figure 8:
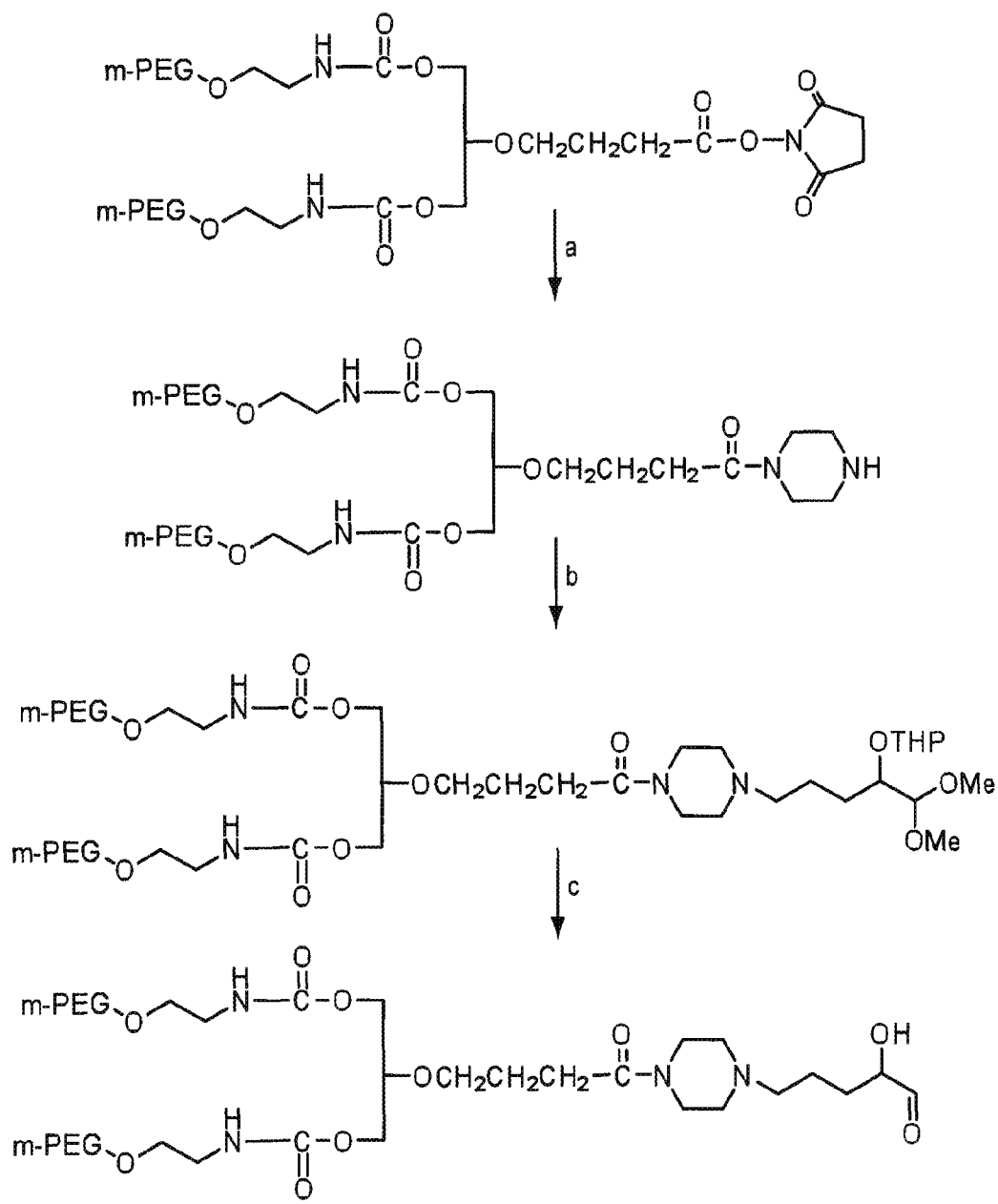
FIG. 8 shows a synthetic scheme for preparation of a branched-PEG reagent of the invention, 5-ruPEG2$_{20K}$-piperazine-2-hydroxy-pentanal (or ruPEG2$_{20K}$-Pip-HP-ALD) (14).

The purified reaction mixture was also analyzed by SDS-PAGE. Thus, the conjugate pools were mixed with sample buffer (NuPAGE LDS 4× buffer, Invitrogen, 10 μL) and loaded on a SDS-PAGE gel (Invitrogen NuPAGE® 4-12% Bis-Tris, running buffer MES 1×) and run at 200 V for 35 min. Similar quantities of conjugate pool were loaded in each lane. The gels were removed, rinsed, stained with SimplyBlue™ SafeStain (Invitrogen) for at least 1 h and then destained for more than 2 h. Results are shown in FIG. 8, with lanes as indicated below:

Lane:

0) Invitrogen Mark12™

1) Lyz+mPEG$_{20K}$-Pip-HP-ALD (12), pH 6.5;

2) Lyz+mPEG$_{20K}$-Pip-HP-ALD (12), pH 7.5;

3) Lyz+mPEG$_{20K}$-Pip-HP-ALD (12), pH 9.0.

Figure 7:
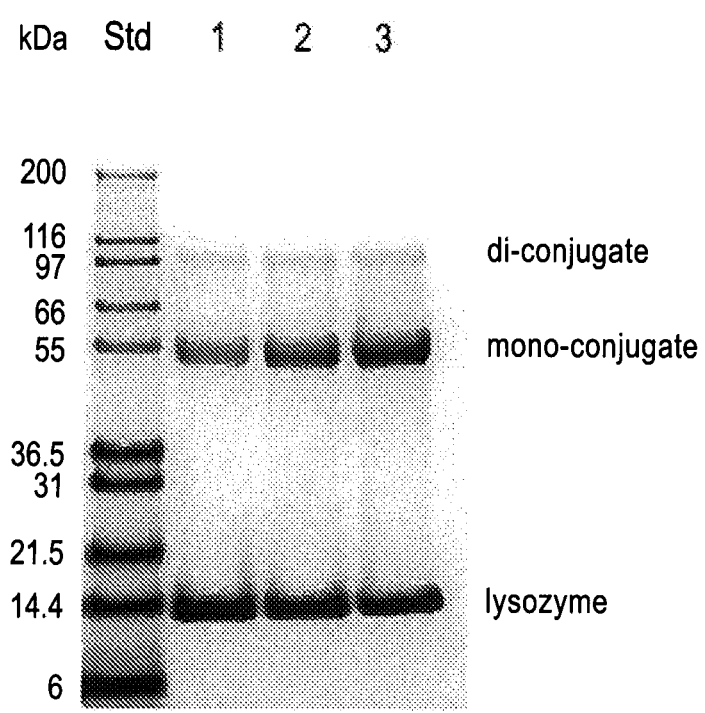
FIG. 7 shows SDS-PAGE gels obtained from electrophoresis of purified reaction mixtures of conjugation reactions of lysozyme (1 mg/mL) with mPEG-aldehyde 20K reagent (50×) at pH 6.5, 7.5, and 9.0, as described in Example 17. Lane:
0) Invitrogen Mark12™
1) Lyz+mPEG$_{20K}$-Pip-HP-ALD (12), pH 6.5;
2) Lyz+mPEG$_{20K}$-Pip-HP-ALD (12), pH 7.5;
3) Lyz+mPEG$_{20K}$-Pip-HP-ALD (12), pH 9.0.

As shown by the results in FIG. 7, increasing levels of mono-conjugate were evident as the pH of the reaction was increased.

Example 18

Preparation of mPEG-5-O-3-deoxyribose Reagent 5-mPEG$_{20K}$-2,4-hydroxy-pentanal or mPEG$_{20K}$-3d-HP-ALD (13)

The following synthetic scheme is employed to prepare the title compound:

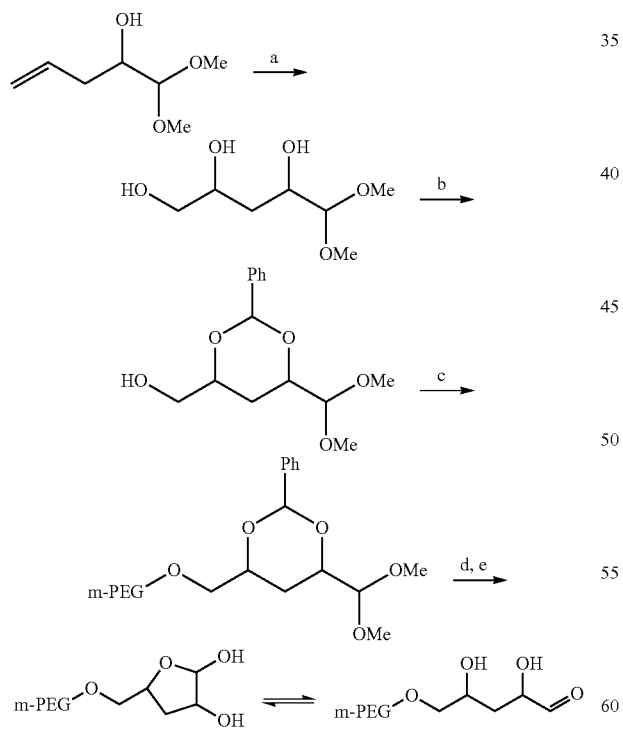

a) OsO$_4$ on polymer, acetone/H$_2$O, 30% H$_2$O$_2$; b) PhCHBr2, pyridine; c) mPEG-OMs 20K, toluene, NaH; d) Pd/C, HOAc, H$_2$,; e) 20% phosphoric acid An alternate route is shown below. The starting material, methyl 3-deoxy-β-D-ribofuranoside, is prepared as described in *J. Am. Chem. Soc.*, 1964, 86(14), 2952.

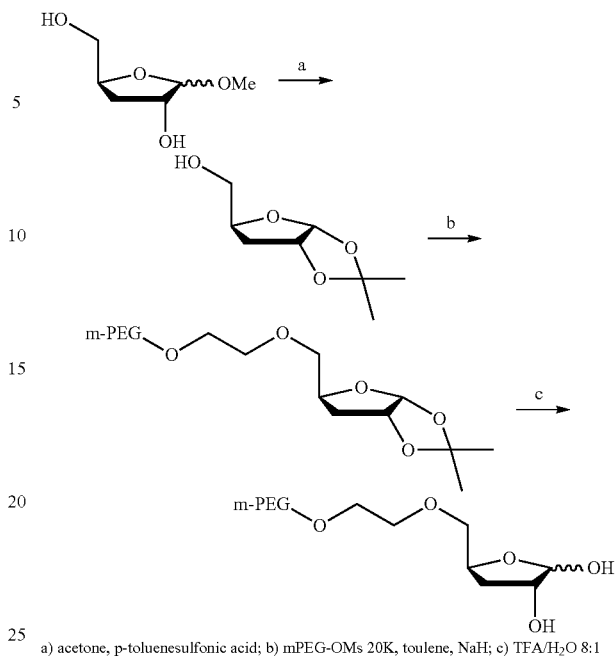

a) acetone, p-toluenesulfonic acid; b) mPEG-OMs 20K, toulene, NaH; c) TFA/H$_2$O 8:1

This reagent can be reacted with a protein or other amine-containing compound, according to procedures described above, to give a stable keto-amine conjugate.

Example 19

Preparation of 5-ruPEG2$_{20K}$-piperazine-2-hydroxy-pentanal (or ruPEG2$_{20K}$-Pip-HP-ALD) (14)

The synthetic scheme shown in FIG. 8 is employed to prepare the title compound. Briefly, the branched PEG reagent ruPEG2$_{20K}$-NHS (which is commercially available from Shearwater Polymers, Inc., Huntsville Ala.) is reacted with piperazine in acetonitrile to provide the piperazine amide (step a). The free ring nitrogen is then reacted with 2-hydroxytetrahydropyranyl-1,1-dimethoxy-pentan-5-methanesulfonate in dioxane/1 M sodium hydroxide to give the protected precursor to the title compound (step b). Deprotection with 1 M sulfuric acid (step c) gives the title reagent (14). This reagent can be reacted with a protein or other amine-containing compound, according to procedures described above, to give a stable keto-amine conjugate.

The invention claimed is:

1. A polymeric reagent having the structure I:

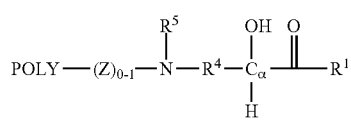

where

R$^1$ is selected from H, lower alkyl, and alkoxyalkyl;

R$^4$ is a two- or three-carbon chain which may be substituted with one or more groups selected from alkyl, alkenyl, aryl, alkoxy, halo, cyano, hydroxy, and a water soluble polymer; wherein the carbon adjacent to Cα is not substituted with hydroxy, and wherein two substituents on $R^4$ may together form an aliphatic or aromatic ring; and
$NR^5$ is a secondary or tertiary amino group which is linked to a water soluble polymer POLY via an optional spacer group Z, where $R^5$ is hydrogen or an alkyl group, which may form a ring with spacer group Z.

2. The reagent of claim 1, having the structure Ia:

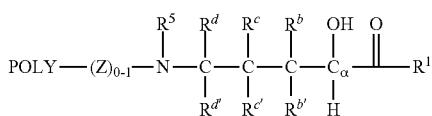

where
$R^1$, $NR^5$, Z and POLY are as defined above,
each of the substituents $R^c$, $R^{c'}$, $R^d$, and $R^{d'}$ is independently selected from hydrogen, alkyl, alkenyl, aryl, alkoxy, halo, cyano, hydroxy, and a water soluble polymer, and each of the substituents $R^b$ and $R^{b'}$ is independently selected from hydrogen, alkyl, alkenyl, aryl, alkoxy, halo, cyano, and a water soluble polymer, wherein at most one of these substituents is a water soluble polymer, and wherein any two of these substituents can together form an aliphatic ring.

3. The reagent of claim 1, wherein $R^1$ is H or methyl.

4. The reagent of claim 3, wherein $R^1$ is H.

5. The reagent of claim 2, wherein said substituents $R^b$, $R^{b'}$, $R^c$, $R^{c'}$, $R^d$, and $R^{d'}$ are independently selected from hydrogen and alkyl, wherein any two such alkyl substituents can together form a 5- to 7-membered aliphatic ring.

6. The reagent of claim 5, wherein two such alkyl substituents on adjacent carbon atoms together form a 5- to 7-membered aliphatic ring.

7. The reagent of claim 2, wherein $R^5$ is lower alkyl.

8. The reagent of claim 7, wherein each of $R^b$, $R^{b'}$, $R^c$, $R^{c'}$, $R^d$, and $R^{d'}$ is hydrogen and $R^5$ is methyl.

9. The reagent of claim 1, wherein Z consists of bonds selected from alkylene, ether, thioether, amide, and amine.

10. The reagent of claim 2, wherein each of $R^b$, $R^{b'}$, $R^c$, $R^{c'}$, $R^d$, and $R^{d'}$ is hydrogen, and $NR^5$ together with Z forms a piperazine ring to which POLY is linked via a ring nitrogen atom.

* * * * *